US008574623B2

(12) United States Patent
Niitsu et al.

(10) Patent No.: US 8,574,623 B2
(45) Date of Patent: *Nov. 5, 2013

(54) THERAPEUTIC AGENT FOR PULMONARY FIBROSIS

(71) Applicant: Nitto Denko Corporation, Ibaraki (JP)

(72) Inventors: Yoshiro Niitsu, Sapporo (JP); Rishu Takimoto, Sapporo (JP); Kenjiro Minomi, Ibaraki (JP); Miyono Miyazaki, Ibaraki (JP); Keiko Kajiwara, Ibaraki (JP); Yasunobu Tanaka, Ibaraki (JP)

(73) Assignee: Nitto Denko Corporation, Ibaraki-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,543

(22) Filed: Oct. 10, 2012

(65) Prior Publication Data

US 2013/0028967 A1 Jan. 31, 2013

Related U.S. Application Data

(63) Continuation of application No. 13/491,976, filed on Jun. 8, 2012, which is a continuation-in-part of application No. 12/933,075, filed as application No. PCT/JP2009/001148 on Mar. 16, 2009, said application No. 13/491,976 is a continuation-in-part of application No. 13/439,330, filed on Apr. 4, 2012, which is a continuation of application No. 11/793,736, filed as application No. PCT/JP2005/023619 on Dec. 22, 2005, now Pat. No. 8,173,170.

(30) Foreign Application Priority Data

Dec. 22, 2004 (JP) .................................. 2004-382791
Mar. 14, 2008 (JP) .................................. 2008-068227

(51) Int. Cl.
*C12N 15/11* (2006.01)
*C07H 21/02* (2006.01)
*C07H 21/04* (2006.01)
*A61K 9/127* (2006.01)
*C12Q 1/68* (2006.01)

(52) U.S. Cl.
USPC .......... 424/450; 435/6.1; 536/23.1; 536/24.5; 514/44

(58) Field of Classification Search
None
See application file for complete search history.

(56) References Cited

U.S. PATENT DOCUMENTS

| 4,966,773 | A | 10/1990 | Gressel et al. |
| 5,472,954 | A | 12/1995 | Loftsson |
| 5,534,261 | A | 7/1996 | Rodgers et al. |
| 5,583,020 | A | 12/1996 | Sullivan |
| 5,643,584 | A | 7/1997 | Farng et al. |
| 5,668,117 | A | 9/1997 | Shapiro |
| 5,733,572 | A | 3/1998 | Unger et al. |
| 5,753,261 | A | 5/1998 | Fernandez et al. |
| 5,785,976 | A | 7/1998 | Westesen et al. |
| 5,811,119 | A | 9/1998 | Mehta et al. |
| 5,820,879 | A | 10/1998 | Fernandez et al. |
| 5,827,886 | A | 10/1998 | Hersh |
| 5,851,538 | A | 12/1998 | Froix et al. |
| 5,919,487 | A | 7/1999 | Simonnet et al. |
| 5,942,230 | A | 8/1999 | Wu et al. |
| 6,037,481 | A | 3/2000 | Zucchetti et al. |
| 6,071,495 | A | 6/2000 | Unger et al. |
| 6,159,591 | A | 12/2000 | Beihoffer et al. |
| 6,177,274 | B1 | 1/2001 | Park et al. |
| 6,180,669 | B1 | 1/2001 | Tamarkin |
| 6,183,774 | B1 | 2/2001 | Aust et al. |
| 6,187,315 | B1 | 2/2001 | Falcon |
| 6,214,345 | B1 | 4/2001 | Firestone et al. |
| 6,217,912 | B1 | 4/2001 | Park et al. |
| 6,238,917 | B1 | 5/2001 | Hendry et al. |
| 6,248,363 | B1 | 6/2001 | Patel et al. |
| 6,251,428 | B1 | 6/2001 | Yoo |
| 6,328,988 | B1 | 12/2001 | Uhrich |
| 6,334,999 | B1 * | 1/2002 | Gilbert et al. ................... 424/45 |
| 6,342,219 | B1 | 1/2002 | Thorpe |
| 6,342,221 | B1 | 1/2002 | Thorpe et al. |
| 6,344,206 | B1 | 2/2002 | Nguyen et al. |
| 6,379,683 | B1 | 4/2002 | Simonnet et al. |
| 6,441,025 | B2 | 8/2002 | Li et al. |
| 6,471,968 | B1 | 10/2002 | Baker, Jr. et al. |
| 6,472,507 | B1 | 10/2002 | Fischer et al. |
| 6,524,583 | B1 | 2/2003 | Thorpe et al. |

(Continued)

FOREIGN PATENT DOCUMENTS

CN 101102795 A 1/2008
EP 0932399 8/1999

(Continued)

OTHER PUBLICATIONS

Agrawal et al., "Antisense therapeutics: Is it as simple as complimentary base recognition?" *Molecular Med. Today* (2000) 6: 72-81.

Andrew et al., "Molecular motion in solid all-trans retinoic acid (vitamin A acid) by protion NMR." *Solid State Nuclear Magnetic Resonance* (1998)13:39-43.

Beljaars et al., "Albumin modified with mannosa 6-phosphate: a potential carrier for selective delivery of antifibrotic drugs to rat and human hepatic stellate cells," *Hepatology*, (1999):29(5):1486-1493.

Benedetti, A. et al., "Inhibition of the Na+/H+ exchanger reduces rat hepatic stellate cell activity and liver fibrosis: an in vitro and in vivo study," *Gastroenterology* (2001)120(2):545-56.

(Continued)

*Primary Examiner* — Doug Schultz
(74) *Attorney, Agent, or Firm* — Knobbe Martens Olson & Bear, LLP

(57) ABSTRACT

Disclosed are: a substance transfer carrier to an extracellular matrix-producing cell in the lung, which comprises a retinoid; a therapeutic agent for pulmonary fibrosis, which utilized the carrier; and a preparation kit of the therapeutic agent.

6 Claims, 10 Drawing Sheets

(56) References Cited

U.S. PATENT DOCUMENTS

| | | | |
|---|---|---|---|
| 6,586,524 B2 | 7/2003 | Sagara | |
| 6,610,841 B1 | 8/2003 | Warren | |
| 6,645,528 B1 | 11/2003 | Straub et al. | |
| 6,652,886 B2 | 11/2003 | Ahn et al. | |
| 6,656,734 B1 | 12/2003 | Bischoff et al. | |
| 6,676,941 B2 | 1/2004 | Thorpe et al. | |
| 6,680,047 B2 | 1/2004 | Klaveness et al. | |
| 6,696,038 B1 | 2/2004 | Mahato et al. | |
| 6,730,334 B2 | 5/2004 | Zhao | |
| 6,740,336 B2 | 5/2004 | Trubetskoy et al. | |
| 6,746,678 B1 | 6/2004 | Shapiro | |
| 6,764,698 B1 | 7/2004 | Byun et al. | |
| 6,838,528 B2 | 1/2005 | Zhao | |
| 6,896,890 B2 | 5/2005 | Singh et al. | |
| 6,908,626 B2 | 6/2005 | Cooper et al. | |
| 6,994,862 B2 | 2/2006 | Jeong et al. | |
| 6,998,115 B2 | 2/2006 | Langer et al. | |
| 7,018,655 B2 | 3/2006 | Lele et al. | |
| 7,045,356 B2 | 5/2006 | Trubetskoy et al. | |
| 7,060,498 B1 | 6/2006 | Wang | |
| 7,064,127 B2 | 6/2006 | Friedman et al. | |
| 7,071,163 B2 | 7/2006 | Sokoloff et al. | |
| 7,074,389 B2 | 7/2006 | Frankenberger et al. | |
| 7,098,030 B2 | 8/2006 | Rozema et al. | |
| 7,101,576 B2 | 9/2006 | Hovey et al. | |
| 7,101,995 B2 | 9/2006 | Lewis et al. | |
| 7,122,202 B2 | 10/2006 | Allen et al. | |
| 7,196,145 B2 | 3/2007 | Ignacious | |
| 7,223,724 B1 | 5/2007 | Alderson et al. | |
| 7,223,837 B2 | 5/2007 | De Groot et al. | |
| 7,262,221 B2 | 8/2007 | Uhrich et al. | |
| 7,265,186 B2 | 9/2007 | Zhao | |
| 7,276,249 B2 | 10/2007 | Ryde et al. | |
| 7,276,348 B2 | 10/2007 | Glick | |
| 7,297,515 B1 | 11/2007 | Szankasi et al. | |
| 7,297,786 B2 | 11/2007 | McCray et al. | |
| 7,316,811 B2 | 1/2008 | Zhao et al. | |
| 7,320,802 B2 | 1/2008 | Ryde et al. | |
| 7,358,223 B2 | 4/2008 | Zhao et al. | |
| 7,404,969 B2 | 7/2008 | Chen et al. | |
| 7,700,541 B2 | 4/2010 | Tanaka et al. | |
| 7,700,542 B2 | 4/2010 | Zhao et al. | |
| 8,003,621 B2 | 8/2011 | Niitsu et al. | |
| 8,173,170 B2 | 5/2012 | Niitsu et al. | |
| 8,178,124 B2 | 5/2012 | Niitsu et al. | |
| 8,258,235 B2 | 9/2012 | Zhao et al. | |
| 2002/0012998 A1 | 1/2002 | Gonda et al. | |
| 2002/0026060 A1 | 2/2002 | Belloni et al. | |
| 2002/0041898 A1 | 4/2002 | Unger et al. | |
| 2002/0143062 A1 | 10/2002 | Lopez-Berestein et al. | |
| 2003/0064094 A1 | 4/2003 | Frankenberger et al. | |
| 2003/0073619 A1 | 4/2003 | Mahato et al. | |
| 2003/0082176 A1* | 5/2003 | LeBowitz et al. | 424/143.1 |
| 2003/0096739 A1 | 5/2003 | Morris | |
| 2003/0147958 A1 | 8/2003 | Ahn et al. | |
| 2003/0161791 A1 | 8/2003 | Bentley et al. | |
| 2003/0211143 A1 | 11/2003 | Liu et al. | |
| 2003/0215395 A1 | 11/2003 | Yu et al. | |
| 2003/0232091 A1* | 12/2003 | Shefer et al. | 424/490 |
| 2004/0028682 A1 | 2/2004 | Border et al. | |
| 2004/0071654 A1 | 4/2004 | Anderson et al. | |
| 2004/0106125 A1 | 6/2004 | Duggan et al. | |
| 2004/0138154 A1 | 7/2004 | Yu et al. | |
| 2004/0142474 A1 | 7/2004 | Mahato et al. | |
| 2005/0004064 A1 | 1/2005 | Tei et al. | |
| 2005/0153337 A1 | 7/2005 | Manoharan | |
| 2005/0165227 A1 | 7/2005 | Vlahov et al. | |
| 2005/0220859 A1 | 10/2005 | Frankenberger et al. | |
| 2005/0256051 A1 | 11/2005 | Morris | |
| 2005/0265961 A1 | 12/2005 | Langer et al. | |
| 2006/0074041 A1 | 4/2006 | Johnston et al. | |
| 2006/0093674 A1 | 5/2006 | Slobodkin et al. | |
| 2006/0127482 A1 | 6/2006 | Fewell et al. | |
| 2006/0147376 A1 | 7/2006 | Yu et al. | |
| 2006/0258751 A1 | 11/2006 | Zhao et al. | |
| 2006/0286033 A1* | 12/2006 | Torday et al. | 424/1.69 |
| 2007/0020761 A1 | 1/2007 | Yu et al. | |
| 2007/0072171 A1 | 3/2007 | Yu et al. | |
| 2007/0243157 A1 | 10/2007 | Tanaka et al. | |
| 2008/0014253 A1 | 1/2008 | Jorgensen et al. | |
| 2008/0145338 A1 | 6/2008 | Anderson et al. | |
| 2008/0193512 A1 | 8/2008 | Niitsu et al. | |
| 2008/0207553 A1 | 8/2008 | Zhao et al. | |
| 2008/0220056 A1 | 9/2008 | Arthur et al. | |
| 2008/0312174 A1 | 12/2008 | Yu et al. | |
| 2009/0105179 A1 | 4/2009 | Yu et al. | |
| 2010/0028416 A1 | 2/2010 | Yu et al. | |
| 2010/0144659 A1 | 6/2010 | Niitsu et al. | |
| 2010/0210715 A1 | 8/2010 | Zhao et al. | |
| 2011/0104255 A1 | 5/2011 | Niitsu et al. | |
| 2011/0229558 A1 | 9/2011 | Niitsu et al. | |
| 2011/0257249 A1 | 10/2011 | Niitsu et al. | |
| 2012/0076852 A1 | 3/2012 | Niitsu | |
| 2012/0189691 A1 | 7/2012 | Niitsu | |
| 2012/0269886 A1 | 10/2012 | Niitsu | |

FOREIGN PATENT DOCUMENTS

| | | |
|---|---|---|
| EP | 1842557 | 10/2007 |
| EP | 2135600 | 12/2009 |
| EP | 2 258 395 A1 | 12/2010 |
| JP | H02-502094 | 7/1990 |
| JP | 5-503076 | 5/1993 |
| JP | B 8-002799 | 1/1996 |
| JP | 8-268906 A1 | 10/1996 |
| JP | 11-269076 | 10/1999 |
| JP | 2002-47211 | 2/2002 |
| JP | 2002-363094 | 12/2002 |
| JP | 2002-371006 A1 | 12/2002 |
| JP | 2003-119138 A1 | 4/2003 |
| JP | 2003-219893 | 8/2003 |
| JP | 2003-528055 A | 9/2003 |
| JP | 2003-528131 | 9/2003 |
| JP | 2004-083436 A | 3/2004 |
| JP | 2004-523236 | 8/2004 |
| JP | 2004-524371 A | 8/2004 |
| JP | 2005-513031 A1 | 5/2005 |
| JP | 2005-531564 | 10/2005 |
| JP | 2005-531628 A1 | 10/2005 |
| JP | 2006-502153 A1 | 1/2006 |
| JP | 2006-506071 | 2/2006 |
| JP | 2009-518372 A | 5/2009 |
| JP | 4533420 | 6/2010 |
| WO | WO 88/06883 | 9/1988 |
| WO | WO 91/04748 | 4/1991 |
| WO | WO 97/33618 | 9/1997 |
| WO | WO 00/57913 A1 | 10/2000 |
| WO | WO 00/64478 | 11/2000 |
| WO | WO 01/68081 A1 | 9/2001 |
| WO | WO 01/72283 | 10/2001 |
| WO | WO 02/44321 | 6/2002 |
| WO | WO 02/066646 | 8/2002 |
| WO | WO 02/083186 A1 | 10/2002 |
| WO | WO 02/092600 | 11/2002 |
| WO | WO 03/009881 | 2/2003 |
| WO | WO 03/045383 | 6/2003 |
| WO | WO 03/080594 A1 | 10/2003 |
| WO | WO 03/097107 | 11/2003 |
| WO | WO 03/097647 | 11/2003 |
| WO | WO 2004/001381 A2 | 12/2003 |
| WO | WO 2004/002489 A1 | 1/2004 |
| WO | WO 2004/019758 A2 | 3/2004 |
| WO | WO 2004/019921 | 3/2004 |
| WO | WO 2004/043239 | 5/2004 |
| WO | WO 2004/065636 | 8/2004 |
| WO | WO 2004/069159 | 8/2004 |
| WO | WO 2004/090108 A2 | 10/2004 |
| WO | WO 2005/082402 | 9/2005 |
| WO | WO 2006/041617 | 4/2006 |
| WO | WO 2006/066001 | 6/2006 |
| WO | WO 2006/068232 | 6/2006 |
| WO | WO 2007/066115 | 6/2007 |
| WO | WO 2007/067417 | 6/2007 |
| WO | WO 2007/104946 A2 | 9/2007 |

(56) References Cited

FOREIGN PATENT DOCUMENTS

| | | |
|---|---|---|
| WO | WO 2007/120479 | 10/2007 |
| WO | WO 2008/006583 A1 | 1/2008 |
| WO | WO 2008/120815 A1 | 10/2008 |
| WO | WO 2008/151150 | 12/2008 |
| WO | WO 2009/036368 | 3/2009 |
| WO | WO 2009/116257 | 9/2009 |
| WO | WO 2010/014117 | 2/2010 |
| WO | WO 2010/026766 | 3/2010 |
| WO | WO 2010/029760 | 3/2010 |

OTHER PUBLICATIONS

Blomhoff, R. et al., "Newly administered [$^3$H] retinol is transferred from hepatocytes to stellate cells in liver for storage," *Experimental Cell Research* (1984) 150:186-193.

Blomhoff, R. et al., "Hepatic uptake of [$^3$H] retinol bound to the serum retinol binding protein involves both parenchymal and perisinusoidal stellate cells," *The Journal of Biological Chemistry* (1985) 260(25): 13571-13575.

Chansri, N. et al., "Inhibition of liver metastasis by all-*trans* retinoic acid incorporated into O/W emulsions in mice," *International Journal of Pharmaceutics* (2006) 321:42-49.

Chirila et al., "The use of synthetic polymers for delivery of therapeutic antisense oligodeoxypucleotides," *Biomaterials* (2002) 23: 321-342.

Choi, et al., "Inhibition of tumor growth by biodegradable microspheres containing all-*trans*-retinoic acid in a human head-and-neck cancer xenograft," *Int. J. Cancer* (2003) 107: 145-148.

Clark, et al. "Cationic lipid-mediated gene transfer: Current concepts," *Curr. Opin. Mol. Ther.* (Apr. 1999) 1(2): 158-176 (abstract only).

Crooke, S.T., "Progress in antisense technology," *Annual Review of Medicine* (2004) 55: 61-95.

Harkevich, D.A., "Pharmacology," *Medicine* (2006): 66-71.

Devi, G. R., "siRNA-based approaches in cancer therapy," *Cancer Gene Therapy* (2006) 13: 819-829.

Dillard, et al., "Retinol decreases β-catenin protein levels in retinoic acid-resistant colon cancer cell lines," *Molecular Carcinogenesis* (2007) 46:315-329.

Dixon, et al., "Nonmenclature of retinoids." *Pure & Appl. Chem.*, (1983) 55(4): 721-726.

Dunham, et al., "Membrane fusion: Studies with a calcium-sensitive dye, arsenazo III, in liposomes," *Proceedings of the National Academy of Science* (Apr. 1977) 74 (4): 1580-1584.

Elbashir, S.M. et al., "Duplexes of 21-nucleotide RNAs mediate RNA interference in cultured mammalian cells," *Nature* (2001) 411:494-498.

Ermak et al., "Monoclonal antibody-directed targeting of fluorescent polystyrene microspheres to Peyer's patch M cells," *Immunology* (1991) 73: 227-280.

Search Report dated Feb. 24, 2011 for European Patent Application No. 09722829.0, filed Mar. 16, 2009.

Extended Search Report dated Jul. 7, 2011 for European Application No. 05819552.0, filed Jul. 18, 2007.

Fallowfield, I. A. et al., "Targeted treatment for cirrhosis," *Expert Opin. Ther. Targets* (Oct. 2004) 8(5):423-35.

Fingl, et al., The pharmacological basis of therapeutics, Fifth Edition, MacMillan Publishing Co, (1975) Cover and contents pages only.

Fire, A. et al., "Potent and specific genetic interference by double-stranded RNA in *Caenorhabditis elegans,*" *Nature* (1998) 391:806-811.

Fortuna, V.A. et al., "Hepatic stellate cells uptake of retinol associated with retinol-binding protein or with bovine serum albumin," *Journal of Cellular Biochemistry* (2003) 90(4):792-805.

Fortunati, et al., "A multi-domain protein for β1 integrin-targeted DNA delivery," *Gene Therapy* (2000) 7:1505-1515.

Friedman, S. L., "Targeting siRNA to arrest fibrosis," *Nature Biotechnology* (Apr. 2008) 26(4): 399-400.

Fuja, T.J. et al., "Trans differentiation of vocal-fold stellate cells and all-*trans* retinol-induced deactivation," *Cell Tissue Res* (2005) 322(3):417-24.

George, J. et al., "In vivo inhibition of rat stellate cell activation by soluble transforming growth factor p type II receptor: A potential new therapy for hepatic fibrosis," *Proc. Nat. Acad. Sci. USA* (Oct. 1999) 96(22):12719-24.

Geubel et al., *Gastroenterology* (Jun. 1991) 100(6): 1701.

Goldberg, et al., "Phase I trial of interferon α2b and liposome-Encapsulated All-*trans* retinoic acid in the treatment of patients with advanced renal cell carcinoma," *Cancer* (Sep. 2002) 95( 5): 1220-1227.

Goodman et al., "Extraction and recombination studies of the interaction of retinol with human plasma retinol-binding protein." *Journal of Lipid Research* (1972) 13: 338-347.

Greene et al, "Protective groups in organic synthesis," John Wiley & Sons, 3rd Edition (1999).

Guo, C., "Vitamin A and chronic obstructive pulmonary disease," Chinese Medicine of Factory and Mine (2008) 21(1):102-103.

Hagiwara, S. et al., "Inhibition of type I procollagen production by tRA va CTE-HSP 47 ribozyme," *J Gene Med.* (2003) 5:784-94.

Hazen, G.G., "The synthesis of nitrogen mustard derivatives of some steroids and related compounds," Dissertation submitted for the degree of Doctor of Philosophy in the University of Michigan, Abstracts (1951) 12(4): 449.

Houglum, et al., "Two different cis-acting regulatory regions direct cell-specific transcription of the collagen a1 (1) gene in hepatic stellate cells and in skin and tendon fibroblasts," *J. Clin. Invest.* (1995) 96: 2269-2276.

Hwang, et al., "Phospholipid-based microemulsion formulation of all-*trans*-retinoic acid for parenteral administration," *International Journal of Pharmaceutics* (2004) 276:175-183.

Iimuro, Y. et al., "Delivery of matrix metalloproteinase-1 attenuates established liver fibrosis in the rat," *Gastroenterology* (2003) 124:445-458.

International Search Report dated Apr. 7, 2009 for International Application No. PCT/JP2009/001148, filed Mar. 16, 2009.

International Preliminary Report on Patentability dated Nov. 2, 2010 for International Application No. PCT/JP2009/001148, filed Mar. 16, 2009.

International Search Report dated Mar. 28, 2006 for International Application No. PCT/JP2005/023619, filed Dec. 22, 2001.

International Preliminary Report on Patentability issued Mar. 26, 2007 for International Application No. PCT/JP2005/023619, filed Dec. 22, 2001.

Jaster, R., "Molecular regulation of pancreatic stellate cell function," *Molecular Cancer* (Oct. 2004) 3(1):26.

Jeong, et al., "Polyion complex micelles composed of all-trans retinoic acid and poly (ethylene glycol)-grafted-chitosan," *Journal of Pharmaceutical Sciences* (Nov. 2006) 95(11): 2348-2360.

Jezequel, A.M. et al., "A morphological study of the early stages of hepatic fibrosis induced by low doses of dimentylnitrosame in the rat," *J. Hepatol.* (Oct. 1987) 5(2): 174-81.

Kamps, J.A.A.M. et al., "Massive targeting ofliposomes, surface-modified with anionized albumins, to hepatic endothelial cells," *Proceedings of the National Academy of Sciences USA* (1997) 94(21):11681-11685.

Kang et al., "Mannose-6 phosphateyinsulin-like growth factor-II receptor is a receptor for retinoic acid," *Proc. Natl. Acad. Sci.* (1998) 95: 13671-13676.

Kikuchi, H., "Liposomes based on nanotechnology. Past, present and future. Part II," *Pharm Tech Japan* (2003) 19(3):419-433.

Kim, et al., "Folate-tethered emulsion for the target delivery of retinoids to cancer cells." *European Journal of Pharmaceutics and Biopharmaceutics* (2008) 68:618-625.

Kim, et al., "Efficient siRNA delivery using water soluble lipopolymer for anti-angiogenic gene therapy," *J. Controlled Release* (2007) 357-363.

Kim, et al., "Retinol-encapsulated low molecular water-soluble chitosan nanoparticles," *International Journal of Pharmaceutics* (Aug. 2006) 319:130-138.

Kircheis, et al., "Tumor targeting with surface-shielded ligand-polycation DNA complexes." *Journal of Controlled Release* (2001) 72:165-170.

Landen, et al., *Cancer Res.* (Aug. 2005) 65(15):6911.

(56) References Cited

OTHER PUBLICATIONS

Li, et al., "Transferrin/Transferrin receptor-mediated drug delivery," *Medicinal Research Reviews* (2002) 22(3):225-253.
Li, D. et al., "Liver fibrogenesis and the role of hepatic stellate cells: New insights and prospects for therapy," *Journal of Gastroenterology and Hepatology* (1999) 14(7):618-633.
Liu, W.B. et al, "Inhibition on the production of collagen type I, III of activated hepatic stellate cells by antisense TIMP-1 recombinant plasmid," *World J. Gastroenterol* (Feb. 2003) 9(2):316-9.
Liébecq, "Biochemical nomenclature and related documents," 2nd Ed. Portland Press (1992): 247-251.
Lim, et al., "Formulation parameters determining the physicochemical characteristics of solid lipid nanoparticles loaded with all-trans retinoic acid," *International Journal of Pharmaceutics* (2002) 243:135-146.
Liu, X.J. et al., "Effects of the tyrosine protein kinase inhibitor genistein on the proliferation, activation of cultured rat hepatic stellate cells," *World J. Gastroenterology.* (Aug. 2002) 8(4):739-45.
Ma, et al., "Comparison of stability for all-trans retinoic acid nanosuspensions and lipid nanoparticle formulations," *International Conference on Complex Medical Engineering* (2007) 197-202.
Madro, A. et al., "The role of pancreatic stellate cells and cytokines in the development of chronic pancreatitis," *Med. Sci. Monit.* (2004) 10(7):RA166-70.
Marcucci, et al., "Active targeting with particulate drug carriers in tumor therapy: fundamentals and recent progress," *Drug Discovery Today* (2004) 9(5):219-228.
Marra, F. et al., "Ligands of peroxisome proliferator-activated receptor y modulate profibrogenic and pro inflammatory actions in hepatic stellate cells," *Gastroenterology* (Aug. 2000) 119(2):466-78.
Massaro, et al., "Noninvasive delivery of small inhibitory RNA and other reagents to pulmonary alveoli in mice," *Am J Physiol Long Cell Mol Physiol* (2004) 287: 1066-1070.
McCaffery, et al., "RNA interference in adult mice," *Nature* (Jul. 2002) 418(6893):38-39.
Miao, et al., "Heat shock protein 47 and pulmonary fibrosis", *International J. Respiration* (2007) 27(22):1745-1747.
Moss, "Biochemical Nomenclature and Related Documents," Portland Press, 2nd Edition (1992) 247-251.
Nastruzzi, et al., "Liposome-associated retinoic acid increased in vitro antiproliferative effects on neoplastic cells" *FEBS Letters* (1990) 259(2):293-296.
Office Action dated Dec. 15, 2009 for Japanese Patent Application No. 2008-068227, filed Mar. 17, 2008.
Office Action dated May 25, 2010 for Japanese Patent Application No. 2008-068227, filed Mar. 17, 2008.
Office Action dated Oct. 26, 2010 for Japanese Patent Application No. 2008-068227, filed Mar. 17, 2008.
Office Action dated Oct. 26, 2011 for Chinese Patent Application No. 200980109550.4, filed Mar. 16, 2009.
Office Action dated May 16, 2012 for U.S. Appl. No. 12/933,075, filed Dec. 10, 2010.
Office Action dated Oct. 24, 2012 for U.S. Appl. No. 13/585,736, filed Aug. 14, 2012.
Office Action dated Oct. 18, 2012 for Chinese Application No. 200980109550.4, filed Mar. 16, 2009.
Office Action dated Sep. 24, 2009, for U.S. Appl. No. 11/793,736, filed Apr. 8, 2008.
Office Action dated Sep. 12, 2011, for U.S. Appl. No. 11/793,736, filed Apr. 8, 2008.
Office Action dated Apr. 13, 2011 for Philippines Patent Application No. 1-2007-501568, filed Dec. 22, 2005.
Office Action dated Jun. 9, 2011 for Indian Patent Application No. 1094/MUMNP/2007, filed Jul. 23, 2007.
Office Action dated May 9, 2011 for Australian Patent Application No. 2005320014, filed Dec. 22, 2005.
Office Action dated Nov. 9, 2011 for European Application No. 05819552.0., filed Dec. 22, 2005.
Office Action dated Oct. 25, 2011 for Indian Patent Application No. 1094/MUMNP/2007, filed Jul. 23, 2007.
Office Action dated Feb. 17, 2012 for Indian Patent Application No. 1094/MUMNP/2007, filed Jul. 23, 2007.
Office Action dated Aug. 28, 2012 for Japanese Application No. 2010-049297, filed Mar. 5, 2010.
Office Action for Russian Patent Application No. 2010142226/15(060672), filed Mar. 16, 2009.
Office Action issued on Aug. 14, 2012 for Japanese Application No. 2009-507561, filed Aug. 9, 2006.
Office Action dated Oct. 29, 2012 for Korean Application No. 10-2007-7015733, filed Dec. 22, 2005.
Opalinska et al., "Nucleic-acid therapeutics: Basic principles and recent applications," *Nature Rev.* (2002) 1: 503-514.
Orr, I.G. et al., "Mechanism of action of the antifibrogenic compound gliotoxin in rat liver cells," *Hepatology* (Jul. 2004) 40(1):232-42.
Pappo, et al., "Monoclonal antibody-directed targeting of fluorescent polystyrene microspheres to Peyer's patch M cells." *Immunology* (1991) 73:277-280.
Park, et al., "Retinol inhibits the growth of all-*trans*-retinoic acid-sensitive and all-*trans*-retinoic acid-resistant colon cancer cells through a retinoic acid receptor-independent mechanism," *Cancer Res.* (Nov. 2005) 65:9923-9933.
Peracchi, et al., "Prospects for antiviral ribozymes and deoxyribozymes," *Rev. Med. Virolo.* (2004) 14: 47-64.
Peterkofsky, et al., "Use of a mixture of proteinase-free collagenases for the specific assay of radioactive collagen in the presence of other proteins," *Biochemistry* (Mar. 1971) 10(6):988-94.
Pinzani, M. et al., "Liver fibrosis: From the bench to clinical targets," *Dig. Liver Dis.* (Apr. 2004) 36(4):231-42.
Qi, Z. et al., "Blockade of type p transforming growth factor signaling prevents liver fibrosis and dysfunction in the rat," *Proc. Natl. Acad. Sci. USA* (Mar. 1999) 96(5):2345-9.
Rees, J.L. et al., *Biochem J.* (May 1989) 259(3):918.
"Remington's Pharmaceutical Sciences," 18th Edition, Mack Publishing Company (1990).
Sakaida et al., "Fibrosis Accelerates the Development of Enzyme-Altered Lesions in the Rat Liver," *Hepatology* Nov. 1998; 28:1247-1252.
Sasaki, H. et al., "Induction of heat shock protein 47 synthesis by TGF-p and IL-1P via enhancement of the heat shock element binding activity of heat shock transcription factor 1," *The Journal of Immunology* (2002)168:5178-5183.
Sato, et al, "Resolution of liver cirrhosis using vitamin A-coupled liposomes to deliver siRNA against a collagen-specific chaperone," *Nature Biotechnology* (2008) 26(4):431-442.
Selman, et al., "Idiopathic pulmonary fibrosis: prevailing and evolving hypotheses about its pathogenesis and implications for therapy," *Ann Intern Med.* (2001) 134:136-151.
Senoo, et al., "Hepatic stellate cells and alveolar septal cells," *Respiration* (1997) 16(4): 604-615.
Senoo, "Studies of the vitamin A-storing (stellate) cell system-from molecules to the arctic area," *Vitamins*, Japan (2006) 80(3): 105-113.
Singh et al., "Liposome encapsulated vitamin A compounds exhibit greater stability and diminished toxicity," *Biophysical Chemistry* (1998) 73: 155-162.
Sioud, M. et al., "Cationic Liposome-mediated delivery of siRNAs in adult mice," *Biochem Biophys Res Commun* (Dec. 26, 2003) 312(4):1221.
Socaciu, et al., "Different ways to insert carotenoids into liposomes affect structure and dynamics of the bilayer differently," *Biophysical Chemistry* (2002) 99: 1-15.
Sun, et al., "Retinoids and their receptors in cancer development and chemoprevention," *Crit. Rev. Onco/Hemato.* (2002) 41: 41-55.
Tabata, et al., "All-trans-retinoic acid prevents radiation- or bleomycin-induced pulmonary fibrosis", *Am J Respir Crit Care Med.* (Dec. 15, 2006) 174(12):1352-60.
Tagami et al., "The gene-slicing effect of siRNA in cationic lipoplexes is enhanced by incorporating pDNA in the complex," *Intl. J Pharmaceutics* (Oct. 2006) 333: 62-69.
Takahashi, et al., "Effects on M5076-heptatic metastasis of retinoic acid and n-(4-hydroxphenyl)retinamide, fenretinide entrapped in sg-liposomes", *Bio. Pharm. Bull.* (2003) 26(7):1060-1063.
Torchilin, V. P. et al., "Immunomicelles: Targeted pharmaceutical carriers for poorly soluble drugs," *PNAS.* (2003) 100(10):6039-6044.

(56) References Cited

OTHER PUBLICATIONS

Torchilin, V. P. "Drug Targeting," *European Journal of Pharmaceutical Sciences.* (2000)11(2):81-91.
Torchilin V. P. "Targeted pharmaceutical nanocarriers for cancer therapy and imaging," *The AAPS Journal* (2007) 9(2):128-47.
Tsuji, H. et al., "Targeting of liposomes surface-modified with glycyrrhizin to the liver. I. Preparation and biological disposition," *Chemical & Pharmaceutical Bulletin* (1991) 39(4):1004-1008.
Office Action dated Mar. 26, 2010 for U.S. Appl. No. 12/210,098, filed Sep. 12, 2008.
Office Action dated Sep. 1, 2010 for U.S. Appl. No. 12/210,098, filed Sep. 12, 2008.
Office Action dated Nov. 18, 2009 for U.S. Appl. No. 12/210,098, filed Sep. 12, 2008.
Ueda et al., "Fibroblasts and their related cells," *Respiration* (1995) 14(7): 708-712.
Ueki, K. et al., "Hepatocyte growth factor gene therapy of liver cirrhosis in rats," *Nat. Med.* (Feb. 1999) 5(2):226-30.
Ui-Tei, K. et al., "Sensitive assay of RNA interference in *Drosphila* and Chinese hamster cultured cells using firefly luciferase gene as target," *FEBS Letters* (2000) 479:79-82.
Viguera et al., "A water-soluble polylysine-retinalddehyde schiff base," *The Journal of Bilogical Chemistry* (1990) 265(5): 2527-2532.
Vogel, S. et al., "An imortalized rat liver stellate cell line (HSC-T6): A new cell model for the study of retinoid metabolism in vitro." *Journal of Lipid Research* (2000) 41: 882-893.
Wang, L. et al., "Effects of herbal compound 861 on human hepatic stellate cell proliferation and activation," *World J. Gastroenterology* (Oct. 2004) 10(19):2831-2835.
Wassall, et al., "Retinoid-phospholipid Interactions as studied by magnetic resonance," *Bulletin of Magnetic Resonance* (1987) 9(3): 85-89.
Watanabe, et al, "Treatment of idiopathic myelofiosis employing siRNA for heat shock protein 7 (siRNA/HSP47) encapsulated in liposomes," *Blood* (2007) 110: 235.
Whitmer, et al., "Membrane-membrane interactions associated with rapid transfer of liposomal bilirubin to microsomal UDP-glucoronyltransferease," *Biochemical Journal* (1987) 244: 41-47.
Winter, et al., "Molecular imaging of angiogenesis in nascent vx-2 rabbit tumors using a novel αvβ3-targeted nanoparticle and 1.5 tesla magnetic resonance imaging," *Cancer Research* (2003) 63:5838-5843.
Wu, J. et al., "Modification of liposomes for liver targeting," *Journal of Hepatology* (1996) 24(6):757-763.
Yoshiji, H. et al., "Angiotensin-II type 1 receptor interaction is a major regulator for liver fibrosis development in rats," *Hepatology* (Oct. 2001)34:745-50.
Zhang et al., "Cationic lipids and polymers mediated vectors for delivery of siRNA," *J. Control Release* (2007) 123: 1-10.
Zhou, H., "A vitamin A-storing cell system," Foreign Medical Sciences (Section of Digestive Disease) (1986) 2: 104-106.
Zimmermann, T.S. et al., *Nature* (May 2006) 441(7089):111-14.
Brash, E. D. and Havre, P. A., "New careers for antioxidants," *Proceedings of the National Academy of Sciences*, (Oct. 2002) 28(1): 30-35.
Saito, M. et al., "Cytotoxicity and apoptosis induction by butylated hydroxyanisole (BHA) and butylated hydroxytoluene (BHT)," *Anticancer Res.* (2003) 23(6C): 4693-701.
Sakagami, H. et al., "Apoptpsis-inducing activity of vitamin C and vitamin K," *Cell Mol. Biol (Noisy-le-grand)* (Feb. 2000) 46(1): 129-43.
Sigounas, G. et al., "dl-alpha-Tocopherol induces apoptosis in erythroleukemia, prostate, and breast cancer cells," *Nutrition and Cancer*, (1997) 28(1): 30-35.
Summons to Attend Oral Proceedings dated Dec. 30, 2012 for European Application No. 05819552.0, filed Jul. 18, 2007.
Szondy, Z. et al., "Induction of apoptosis by retinoids and retinoic acid receptorg-selective compounds in mouse thymocytes through a novel apoptosis pathway," *Molecular Pharmacology* (1997) 51: 972-82.
Office Action issued on May 9, 2013 in Chinese Patent Application No. 201110316481.3, filed Dec. 22, 2005.
Office Action issued on May 15, 2013 in Taiwanese Patent Application No. 098108655, filed Mar. 17, 2009.
English translation of an Office Action in Russian Patent Application No. 2010142226/15(060672), filed Mar. 16, 2009.
Harkevich, D.A., "Pharmacology" Medicine (2006): 66-71.
Examination Report dated May 27, 2013 for Australian Patent Application No. 2009227445, filed on Mar. 17, 2009.
Final Rejection dated May 21, 2013 in Japanese Patent Application No. 2011-013933, filed on Jan. 26, 2011.
Notification of the 3$^{rd}$ Office Action dated Jun. 24, 2013, in Chinese Patent Application No. 200980109550.4, filed on Jan. 26, 2011.
Office Action date Feb. 19, 2013 for Japanese Patent application No. 2011-013933, filed on Jan. 26, 2011.

* cited by examiner

SEQUENCE LISTING

<160> NUMBER OF SEQ ID NOS: 10

<210> SEQ ID NO 1
<211> LENGTH: 27
<212> TYPE: RNA
<213> ORGANISM: Artificial Sequence
<220> FEATURE:
<223> OTHER INFORMATION: Sense strand of gp46siRNAseqA

<400> SEQUENCE: 1
guuccaccau aagaugguag acaacag                              27

<210> SEQ ID NO 2
<211> LENGTH: 27
<212> TYPE: RNA
<213> ORGANISM: Artificial Sequence
<220> FEATURE:
<223> OTHER INFORMATION: Antisense strand of gp46siRNAseqA

<400> SEQUENCE: 2 guugcuacc aucuuauggu ggaacau                               27

<210> SEQ ID NO 3
<211> LENGTH: 27
<212> TYPE: RNA
<213> ORGANISM: Artificial Sequence
<220> FEATURE:
<223> OTHER INFORMATION: Sense strand of gp46siRNAseqB

<400> SEQUENCE: 3
ccacaaguuu uauauccaau cuagcag                              27

<210> SEQ ID NO 4
<211> LENGTH: 27
<212> TYPE: RNA
<213> ORGANISM: Artificial Sequence
<220> FEATURE:
<223> OTHER INFORMATION: Antisense strand of gp46siRNAseqB

<400> SEQUENCE: 4
gcuagauugg auauaaaacu uguggau                              27

<210> SEQ ID NO 5
<211> LENGTH: 27
<212> TYPE: RNA
<213> ORGANISM: Artificial Sequence
<220> FEATURE:
<223> OTHER INFORMATION: Sense strand of gp46siRNAseqC

<400> SEQUENCE: 5
cuagagccau uacauuacau ugacaag                              27

<210> SEQ ID NO 6
<211> LENGTH: 27
<212> TYPE: RNA
<213> ORGANISM: Artificial Sequence
<220> FEATURE:
<223> OTHER INFORMATION: Antisense strand of gp46siRNAseqC

<400> SEQUENCE: 6
ugucaaugua auguaauggc ucuagau                              27

<210> SEQ ID NO 7
<211> LENGTH: 27
<212> TYPE: RNA

```
<213> ORGANISM: Artificial Sequence
<220> FEATURE:
<223> OTHER INFORMATION: Sense strand of random siRNA

<400> SEQUENCE: 7
cgauucgcua gaccggcuuc auugcag                                              27

<210> SEQ ID NO 8
<211> LENGTH: 27
<212> TYPE: RNA
<213> ORGANISM: Artificial Sequence
<220> FEATURE:
<223> OTHER INFORMATION: Antisense strand of random siRNA

<400> SEQUENCE: 8
gcaaugaagc cggucuagcg aaucgau                                              27

<210> SEQ ID NO 9
<211> LENGTH: 19
<212> TYPE: RNA
<213> ORGANISM: Artificial Sequence
<220> FEATURE:
<223> OTHER INFORMATION: Artificially synthesized RNA molecule
<220> FEATURE:
<221> NAME/KEY: misc_feature
<222> LOCATION: 1
<223> OTHER INFORMATION: n = G with an inverted 1,2 dideoxy-D-Ribose
<220> FEATURE:
<221> NAME/KEY: misc_feature
<222> LOCATION: 19
<223> OTHER INFORMATION: n = A with a 1,3-propanediol spacer and a
      phosphate on 3' terminus

<400> SEQUENCE: 9
nagacacaug ggugcuaun                                                       19

<210> SEQ ID NO 10
<211> LENGTH: 20
<212> TYPE: RNA
<213> ORGANISM: Artificial Sequence
<220> FEATURE:
<223> OTHER INFORMATION: Artificially synthesized RNA molecule
<220> FEATURE:
<221> NAME/KEY: misc_feature
<222> LOCATION: 20
<223> OTHER INFORMATION: n = methylcytosine linked to two
      1,3-propanediol spacers.

<400> SEQUENCE: 10
uauagcaccc augugucucn                                                      20
```

THERAPEUTIC AGENT FOR PULMONARY FIBROSIS

RELATED APPLICATIONS

This application is a continuation of U.S. Ser. No. 13/491,976, filed Jun. 8, 2012, which is a continuation-in-part of U.S. Ser. No. 12/933,075, filed Dec. 10, 2010, which is a national stage filing under 35 U.S.C. §371 of international application PCT/JP2009/001148, filed Mar. 16, 2009. U.S. Ser. No. 13/491,976 is also a continuation-in-part of U.S. Ser. No. 13/439,330, filed Apr. 4, 2012, which is a continuation of U.S. Ser. No. 11/793,736, filed Apr. 8, 2008, now U.S. Pat. No. 8,173,170, issued May 8, 2012, which is a national stage filing under 35 U.S.C. §371 of international application PCT/JP2005/023619, filed Dec. 22, 2005. The disclosures of all of the above are hereby incorporated by reference in their entireties for all purposes.

SEQUENCE LISTING

The present application is being filed along with a Sequence Listing in electronic format. The Sequence Listing is provided as a file entitled KUZU1_010P1C1_SEQ.TXT, created Sep. 25, 2012, which is 3 KB in size. The information in the electronic format of the Sequence Listing is incorporated herein by reference in its entirety.

BACKGROUND OF THE INVENTION

1. Field of the Invention

The present invention relates to a substance delivery carrier targeted at extracellular matrix-producing cells in the lung, and a therapeutic agent for pulmonary fibrosis and a method for treating pulmonary fibrosis utilizing the carrier.

2. Description of the Related Art

Pulmonary fibrosis is a disease characterized by diffuse fibroplasia of the alveolar walls, and its main symptoms include dry cough and dyspnea on exertion. In a restricted sense, it refers to end-stage disease states of interstitial pneumonia; while in a broad sense, it means a co-existing state of pulmonary fibrosis in a restricted sense with interstitial pneumonia. Any interstitial pneumonia can cause pulmonary fibrosis. Interstitial pneumonia is a generic term for the diseases that induce inflammation in interstices of the lung (including alveolar septum in a restricted sense, and intralobular interstice and the vicinity of pleural membrane in a broad sense); it includes those induced by a specific cause such as infection, collagen disease, radiation, drug, and dust, and those without any known cause, i.e., idiopathic interstitial pneumonia. Idiopathic interstitial pneumonia is further classified as follows based on the findings of video-assisted thoracoscopic surgery (VATS) and high-resolution computer tomography (HRCT): idiopathic pulmonary fibrosis (IPF), nonspecific interstitial pneumonia (NSIP), acute interstitial pneumonia (AIP), cryptogenic organizing pneumonia (COP), respiratory bronchiolitis-associated interstitial lung disease (RB-ILD), desquamative interstitial pneumonia (DIP), lymphoid interstitial pneumonia (LIP), etc. Many of the interstitial pneumonia with specified causes are cured by elimination of the causes and administration of anti-inflammatory agents such as steroid drugs. However, regarding idiopathic interstitial pneumonia, there is no radical treatment method to date, and only treatments such as administration of steroid drugs, azathioprine and cyclophosphamide during exacerbation of symptoms, and oxygen therapy during development of hypoxemia are performed; accordingly, there are many dead cases in which idiopathic interstitial pneumonia progresses into pulmonary fibrosis. Therefore, the average survival period after establishment of diagnosis of idiopathic interstitial pneumonia is as short as 2.5-5 years, and this disease is designated as one of the specific diseases in Japan.

Under such circumstances, much research effort has been made to the development of therapeutic agents for pulmonary fibrosis. As a result, pharmaceutical agents such as colchicine, D-penicillamine, pirfenidone (5-methyl-1-phenyl-2-[1H]-pyridone), interferon-β1a, relaxin, lovastatin, beractant, N-acetylcysteine, keratinocyte growth factor, captopril (Non Patent Literature 1), hepatocyte growth factor (Patent Literature 1), Rhokinase inhibitor (Patent Literature 2), thrombomodulin-like protein (Patent Literature 3), bilirubin (Patent Literature 4), PPARγ (peroxisome proliferator-activated receptor gamma) activator (Patent Literature 5), imatinib (Patent Literature 6), interferon-γ (Patent Literature 7) have been reported to show some effectiveness in animal models of pulmonary fibrosis or clinical trials. However, none of these agents is not yet satisfactory, and further development of the therapeutic agents for pulmonary fibrosis has been awaited.

CITATION LIST

Patent Literature 1: JP A No. 8-268906
Patent Literature 2: WO 00/57913
Patent Literature 3: JP A No. 2002-371006
Patent Literature 4: JP A No. 2003-119138
Patent Literature 5: JP A No. 2005-513031
Patent Literature 6: JP A No. 2005-531628
Patent Literature 7: JP A No. 2006-502153
Patent Literature 8: WO 2006/068232
Non Patent Literature 1: Ann Intern Med. 2001; 134(2): 136-51

The above Patent Literature and Non Patent Literature, and all other references referred to herein, are hereby incorporated by reference in their entireties for all purposes.

SUMMARY OF THE INVENTION

Problems to be Solved by the Invention

An object of the present invention is to provide a carrier that can deliver a substance such as drugs specifically to extracellular matrix-producing cells in the lung, as well as a therapeutic agent for pulmonary fibrosis and a method for treating pulmonary fibrosis utilizing said carrier.

Means for Solving the Problems

The inventors of the present invention have searched for novel therapeutic agents for pulmonary fibrosis, and found that the administration of a composition in which a carrier comprising a retinoid carries an inhibitor for the production of extracellular matrix can effectively treat pulmonary fibrosis; then the inventors have completed this invention.

While it has been known that a carrier comprising vitamin A can deliver a drug to stellate cells that store vitamin A (refer to Patent Literature 8), the relationship with pulmonary fibrosis has been completely unknown to date.

Namely, the present invention relates to the following:

(1) A substance delivery carrier to an extracellular matrix-producing cell in the lung, comprising a retinoid as a targeting agent.

(2) The carrier according to the above (1), wherein the retinoid derivative comprises retinol.

(3) The carrier according to the above (1) or (2), wherein the retinoid content is 0.2-20 wt % of the entire carrier.

(4) The carrier according to any one of the above (1) to (3), wherein the carrier has a form of liposome, and the molar ratio of the retinoid to the lipid contained in the liposome is 8:1-1:4.

(5) A composition for treating pulmonary fibrosis, comprising the carrier according to any one of the above (1) to (4) and a drug that controls the activity or growth of extracellular matrix-producing cells in the lung.

(6) The composition according to the above (5), wherein the drug that controls the activity or growth of extracellular matrix-producing cells in the lung is selected from the group consisting of an agent for inhibiting activity or production of a bioactive substance selected from the group consisting of gelatinase A, gelatinase B and angiotensinogen, an inhibitor of cell activity, a growth inhibitor, an apoptosis-inducing agent, as well as an siRNA (small interfering RNA), a ribozyme, an anti-sense nucleic acid, and a DNA/RNA chimeric polynucleotide which target at least one of extracellular matrix constituent molecules or molecules involved in the production or secretion of said extracellular matrix constituent molecules, and a vector that expresses said siRNA, ribozyme, anti-sense nucleic acid, and DNA/RNA chimeric polynucleotide.

(7) The composition according to the above (6), wherein the molecule involved in the production or secretion of the extracellular matrix constituent molecules is HSP (heat shock protein) 47.

(8) The composition according to any one of the above (5) to (7), wherein the drug and the carrier are mixed at a place of medical treatment or in its vicinity.

(9) A kit for preparing the composition according to any one of the above (5) to (8), wherein the kit comprises one or more containers comprising singly or in combination a drug for inhibiting activity or growth of extracellular matrix-producing cells in the lung, a retinoid, and if necessary, a carrier-constituent substance other than retinoid.

Effects of the Invention

While the exact mechanism of action of the composition for treating pulmonary fibrosis of the present invention has not yet been completely clarified, the mechanism is considered as follows: with the composition, retinoid functions as a targeting agent to extracellular matrix-producing cells in the lung such as fibroblasts and myofibroblasts, and the retinoid delivers an active ingredient such as pharmaceutical agents that control activity or growth of extracellular matrix-producing cells in the lung to such cells, thereby exhibiting the effect against pulmonary fibrosis.

Accordingly, since active ingredients can be efficiently delivered to action sites, and further to targeted cells by using the carrier of the present invention, the treatment, suppression of progression, and prevention of onset of pulmonary fibrosis, in particular idiopathic interstitial pneumonia the treatment of which has been difficult to date are made possible; thus, the inventive carrier significantly contributes to the human medicine and veterinary medicine.

Moreover, the carrier of the present invention can be combined with any pharmaceutical drugs (for example, existing therapeutic agents for pulmonary fibrosis) to increase their action efficiency; therefore, it is also advantageous as its application range in terms of formulation is broad, facilitating the production of effective therapeutic agents.

DETAILED DESCRIPTION OF THE PREFERRED EMBODIMENTS

Figure 1:
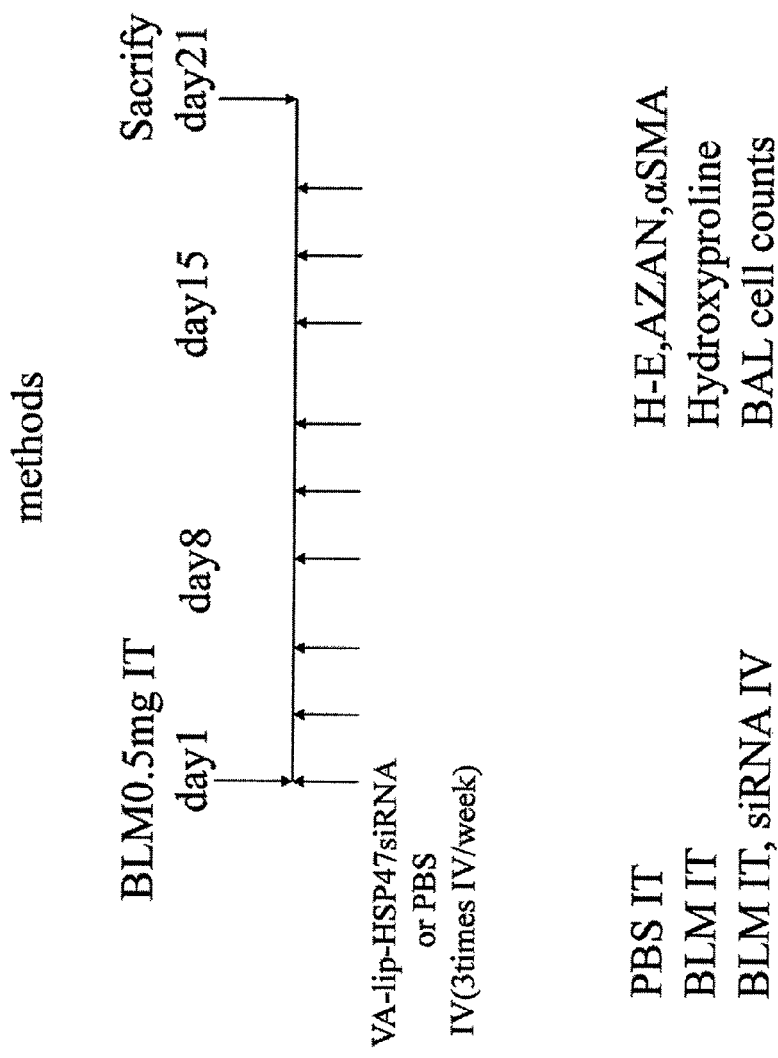
FIG. 1 is a schematic diagram showing induction of pulmonary fibrosis in rats and drug-administration schedule.

In the present invention, the extracellular matrix-producing cells in the lung are not particularly limited as long as they are cells present in the lung and having a capability of producing extracellular matrix, and they include, for example, fibroblasts and myofibroblasts present in the lung. Fibroblasts present in the lung include, for example, vascular adventitial fibroblasts and bronchiolar adventitial fibroblasts, etc. Myofibroblasts present in the lung may include not only those derived from such fibroblasts present in the lung, but also those derived from fibroblasts in the circulating blood and those transformed from endothelial cells by endothelial mesenchymal transdifferentiation. Myofibroblasts are characterized by expression of α-smooth muscle actin (α-SMA). The myofibroblasts in the present invention are those identified, e.g., by immunostaining using detectably-labeled anti-α-SMA antibodies. In addition, while fibroblasts express vimentin that is characteristic to mesenchymal cells, they do not express α-SMA; therefore, fibroblasts can be identified by double-staining with vimentin and α-SMA.

The retinoid of the present invention is not particularly limited as long as it promotes delivery of a substance to extracellular matrix-producing cells in the lung, and examples thereof include retinoid derivatives such as retinol (vitamin A), etretinate, tretinoin, isotretinoin, adapalene, acitretine, tazarotene, and retinol palmitate, as well as vitamin A analogues such as fenretinide (4-HPR, 4-hydroxyphenylretinamide) and bexarotene.

The retinoid of the present invention is that which promotes specific delivery of a substance to extracellular matrix-producing cells in the lung. The mechanism of the promotion of substance delivery by retinoid has not yet been completely clarified; however, the following mechanism is considered:

for example, a retinoid which has specifically bound to a retinol-binding protein (RBP) is taken into an extracellular matrix-producing cell in the lung through a certain receptor present on the surface of this cell.

A retinoid is a member of the class of compounds having a skeleton in which four isoprenoid units are bonded in a head-to-tail manner (see G. P. Moss, "Biochemical Nomenclature and Related Documents," 2nd Ed. Portland Press, pp. 247-251 (1992)). Vitamin A is a generic descriptor for a retinoid that qualitatively shows the biological activity of retinol. Retinoid that can be used in the present invention are not particularly limited, and examples thereof include retinoid derivatives such as retinol, retinal, retinoic acid, an ester of retinol and a fatty acid, an ester of an aliphatic alcohol and retinoic acid, etretinate, tretinoin, isotretinoin, adapalene, acitretine, tazarotene and retinol palmitate, and vitamin A analogues such as fenretinide (4-HPR) and bexarotene.

Of these, retinol, retinal, retinoic acid, an ester of retinol and a fatty acid (such as retinyl acetate, retinyl palmitate, retinyl stearate and retinyl laurate) and an ester of an aliphatic alcohol and retinoic acid (such as ethyl retinoate) are preferable from the viewpoint of efficiency of specific delivery of a substance to extracellular matrix-producing cells in the lung.

All retinoid isomers, such as cis-trans, are included in the scope of the present invention. The retinoid may be substituted with one or more substituents. The retinoid in the present invention includes a retinoid in an isolated state as well as in a solution or mixture state with a medium that can dissolve or retain the retinoid.

The carrier of the present invention may be formed from the retinoid on its own or may be formed by making the retinoid bind to or enclosed in a carrier constituent component other than the retinoid. Therefore, the carrier of the present invention may comprise a carrier constituent component other than the retinoid. Such a component is not particularly limited, and any component known in the medicinal and pharmaceutical fields may be used, but those that can enclose retinoid or can bind thereto are preferable.

Examples of such a component include a lipid, for example, a phospholipid such as glycerophospholipid, a sphingolipid such as sphingomyelin, a sterol such as cholesterol, a vegetable oil such as soybean oil or poppy seed oil, a mineral oil, and a lecithin such as egg-yolk lecithin, but the examples are not limited thereto. Among them, those that can form a liposome are preferable, for example, a natural phospholipid such as lecithin, a semisynthetic phospholipid such as dimyristoylphosphatidylcholine (DMPC), dipalmitoylphosphatidylcholine (DPPC), or distearoylphosphatidylcholine (DSPC), and dioleylphosphatidylethanolamine (DOPE), dilauroylphosphatidylcholine (DLPC), and cholesterol.

A particularly preferred component is a component that can avoid capture by the reticuloendothelial system, and examples thereof include cationic lipids such as N-(α-trimethylammonioacetyl)-didodecyl-D-glutamate chloride (TMAG), N,N',N'',N'''-tetramethyl-N,N',N'',N'''-tetrapalmitylspermine (TMTPS), 2,3-dioleyloxy-N-[2(sperminecarboxamido)ethyl]-N,N-dimethyl-1-propanaminium trifluoroacetate (DOSPA), N-[1-(2,3-dioleyloxy)propyl]-N,N,N-trimethylammonium chloride (DOTMA), dioctadecyldimethylammonium chloride (DODAC), didodecylammonium bromide (DDAB), 1,2-dioleyloxy-3-trimethylammoniopropane (DOTAP), 3β-[N—(N',N'-dimethylaminoethane)carbamoyl]cholesterol (DC-Chol), 1,2-dimyristoyloxypropyl-3-dimethylhydroxyethylammonium (DMRIE), and O,O'-ditetradecanoyl-N-(α-trimethylammonioacetyl)diethanolamine chloride (DC-6-14).

The binding of the retinoid to the carrier of the present invention or the enclosing of it therein is also possible by binding or enclosing the retinoid to or in a constituent component, other than the retinoid, of the carrier by a chemical and/or physical method. Alternatively, the binding or enclosing the retinoid to or in the carrier of the present invention can also be carried out by mixing the retinoid and a constituent component, other than the retinoid, of the carrier when preparing the carrier. The amount of retinoid bound to or enclosed in the carrier of the present invention may be, as a weight ratio in the carrier constituent components, 0.01% to 100%, preferably 0.2% to 20%, and more preferably 1% to 5%. The binding or enclosing of retinoid to or in the carrier may be performed before a drug, etc. is carried on the carrier, may be performed by simultaneously mixing the carrier, a retinoid derivative and a drug, etc., or may be performed by mixing a retinoid derivative with a carrier on which a drug, etc. is already carried. Therefore, the present invention also relates to a process for producing a formulation specific to extracellular matrix-producing cells in the lung, the process including a step of binding a retinoid to any existing drug binding carrier or drug encapsulating carrier, for example, a liposomal formulation such as DaunoXome®, Doxil, Caelyx®, or Myocet®.

The form of the carrier of the present invention may be any form as long as a desired substance or matter can be transported to a target extracellular matrix-producing cell in the lung, and although not limited thereto, examples thereof include a macromolecular micelle, a liposome, an emulsion, microspheres, and nanospheres. In the present invention, from the viewpoint of high delivery efficiency, wide selection of substances to be delivered, and ease of making a formulation, etc., a liposomal form is preferable among the forms, and a cationic liposome that includes a cationic lipid is particularly preferable. In the case that the carrier is a liposomal form, the molar ratio of the retinoid to liposome constituent components other than the retinoid is, considering the efficiency of retinoid's binding to or enclosing in the carrier, preferably 8:1 to 1:4, more preferably 4:1 to 1:2, yet more preferably 3:1 to 1:1, and particularly preferably 2:1.

The carrier of the present invention may contain a substance to be transported within its interior, may be attached to the exterior of a substance to be transported, or may be mixed with a substance to be transported, as long as retinoid contained therein is present in such a form that it can function as a targeting agent. "Function as a targeting agent" referred to here means that the carrier containing retinoid reaches and/or is taken up by the target cell, i.e., extracellular matrix-producing cells in the lung, more rapidly and/or in a larger quantity than with a carrier not containing retinoid, and this may easily be confirmed by, for example, adding a labeled or label-containing carrier to a culture of target cells, and analyzing the sites where the label is present after a predetermined period of time. Structurally, this requirement can be satisfied, for example, if retinoid is at least partially exposed to the exterior of a formulation containing the carrier at the latest by the time it reaches the target cell. Whether or not the retinoid is exposed at the exterior of a formulation can be evaluated by contacting the formulation to a substance that specifically binds to retinoid, such as a retinol-binding protein (RBP), and evaluating the binding to the formulation.

The substance or matter that is delivered by the present carrier is not particularly limited, and it preferably has a size such that it can physically move within the body of a living being from an administration site to a lesion site where a target cell is present. Therefore, the carrier of the present invention can transport not only a substance such as an atom, a molecule, a compound, a protein, or a nucleic acid, but also a matter such as a vector, a virus particle, a cell, a drug-releasing system formed from one or more elements, or a micromachine. The above substance or matter preferably has the property of having some influence on a target cell, and examples thereof include those that label a target cell and those that control (e.g. increase or suppress) the activity or growth of a target cell.

Therefore, in one embodiment of the present invention, the substance that the carrier delivers is "a drug controlling the activity or growth of an extracellular matrix-producing cell in the lung". The activity of an extracellular matrix-producing cell in the lung referred to here indicates various activities such as secretion, uptake, migration, etc. exhibited by an extracellular matrix-producing cell in the lung, and in the present invention among them it typically means, in particular, activities involved in the onset, progression, and/or recurrence of pulmonary fibrosis. Examples of such activities include, but are not limited to, production/secretion of a bioactive substance such as gelatinase A and gelatinase B (MMP (matrix metalloproteinase) 2 and MMP 9, respectively) and angiotensinogen, etc., and an extracellular matrix component such as collagen, proteoglycan, tenascin, fibronectin, thrombospondin, osteopontin, osteonectin, and elastin.

Therefore, the drug controlling the activity or growth of an extracellular matrix-producing cell in the lung may be any drug that directly or indirectly suppresses the physical, chemical, and/or physiological actions, etc. of said cell related to the onset, progression, and/or recurrence of pulmonary fibrosis, and while not being limited thereto, it includes the following: drugs inhibiting the activity or production of the above bioactive substances, MMP inhibitors such as batimastat, and antibodies and antibody fragments that neutralize the above bioactive substances, and substances that suppress expression of the above bioactive substances, such as an siRNA, a ribozyme, an antisense nucleic acid (including RNA, DNA, PNA (peptide nucleic acid), or a composite thereof), and substances that have a dominant negative effect such as a dominant negative mutant, or a vector expressing the same, drugs suppressing the production and secretion of the above extracellular matrix component, etc., for example, substances that suppress expression of the extracellular matrix component, such as an siRNA, a ribozyme, an antisense nucleic acid (including RNA, DNA, PNA, or a composite thereof), and substances that have a dominant negative effect such as a dominant negative mutant, or a vector expressing the same, inhibitors of cell activity such as a sodium channel blocker, cell-growth inhibitors, for example alkylating agents (such as ifosfamide, nimustine, cyclophosphamide, dacarbazine, melphalan, and ranimustine), antitumor antibiotics (such as idarubicin, epirubicin, daunorubicin, doxorubicin, pirarubicin, bleomycin, peplomycin, mitoxantrone, and mitomycin C), antimetabolites (such as gemcitabine, enocitabine, cytarabine, tegafur/uracil, a tegafur/gimeracil/oteracil potassium mixture, doxifluridine, hydroxycarbamide, fluorouracil, methotrexate, and mercaptopurine), alkaloids such as etoposide, irinotecan, vinorelbine, docetaxel hydrate, paclitaxel, vincristine, vindesine, and vinblastine, and platinum complexes such as carboplatin, cisplatin, and nedaplatin, and apoptosis inducers such as compound 861, gliotoxin, lovastatin, and Beractant. Furthermore, the "drug controlling the activity or growth of an extracellular matrix-producing cell in the lung" in the present invention may be any drug that directly or indirectly promotes the physical, chemical, and/or physiological actions, etc. of an extracellular matrix-producing cell in the lung directly or indirectly related to the suppression of onset, progression, and/or recurrence of pulmonary fibrosis.

The substance delivered by the carrier of the invention include, without limitation, drugs other than those mentioned above and which suppress the onset, progression, and/or recurrence of pulmonary fibrosis, and examples include, but are not limited to, colchicine, D-penicillamine, pirfenidone (5-methyl-1-phenyl-2-[1H]-pyridone), interferon-β1a, relaxin, N-acetylcysteine, keratinocyte growth factor, captopril, hepatocyte growth factor, Rho kinase inhibitor, thrombomodulin-like protein, bilirubin, PPARγ activator, imatinib, interferon-γ, and TGF β receptor kinase inhibitor.

The substance or matter delivered by the carrier of the present invention may or may not be labeled. Labeling enables monitoring of the success or failure of transport, increases and decreases in target cells, etc., and is particularly useful at the testing/research level. A label may be selected from any label known to a person skilled in the art such as, for example, any radioisotope, magnetic material, substance that binds to a labeling substance (e.g. an antibody), fluorescent substance, fluorophore, chemiluminescent substance, and enzyme, etc.

In the present invention, "for an extracellular matrix-producing cell in the lung" or "for the delivery to an extracellular matrix-producing cell in the lung" means that it is suitable to use to extracellular matrix-producing cells as a target, and this includes it being possible to deliver a substance to this cell, more rapidly, efficiently, and/or in a larger quantity than to other cells, for example, normal cells. For example, the carrier of the present invention can deliver a substance to an extracellular matrix-producing cell in the lung at a rate and/or efficiency of 1.1 times or more, 1.2 times or more, 1.3 times or more, 1.5 times or more, 2 times or more, or even 3 times or more compared with other cells.

The present invention also relates to a composition for controlling the activity or growth of an extracellular matrix-producing cell in the lung, or for treating pulmonary fibrosis, that comprises the carrier, and the drug controlling the activity or growth of an extracellular matrix-producing cell in the lung, and to a use of the carrier in the production of such compositions.

In the present invention, pulmonary fibrosis includes not only pulmonary fibrosis in a restricted sense, but also pulmonary fibrosis in a broad sense that includes co-existence of interstitial pneumonia. The pulmonary fibrosis of the present invention can be caused by any interstitial pneumonia, for example, infectious interstitial pneumonia associated with viral pneumonia, fungal pneumonia, mycoplasmal pneumonia, etc., interstitial pneumonia associated with collagen disease such as rheumatoid arthritis, systemic scleroderma, dermatomyositis, polymyositis, mixed connective-tissues disease (MCTD), etc., interstitial pneumonia associated with radiation exposure, drug-induced interstitial pneumonia caused by anticancer agents such as bleomycin, herbal medicines such as Sho-sai-ko-to, interferon, antibiotics, paraquat, etc., and idiopathic interstitial pneumonia such as idiopathic pulmonary fibrosis, nonspecific interstitial pneumonia, acute interstitial pneumonia, cryptogenic organizing pneumonia, respiratory bronchiolitis-associated interstitial lung disease, desquamative interstitial pneumonia, lymphoid interstitial pneumonia, etc., and accordingly, it also includes chronic states of such interstitial pneumonia. The pulmonary fibrosis of the present invention preferably includes chronic states of drug-induced interstitial pneumonia and idiopathic interstitial pneumonia.

In the composition of the present invention, as long as the retinoid contained in the carrier is present in a mode that functions as a targeting agent, the carrier may contain a substance to be delivered within its interior, may be attached to the exterior of a substance to be delivered, or may be mixed with a substance to be delivered. Therefore, depending on the administration route and the manner in which the drug is released, etc., the composition may be covered with an appropriate material such as, for example, an enteric coating or a material that disintegrates over time, or may be incorporated into an appropriate drug release system.

The composition of the present invention may be administered via various routes including both oral and parenteral routes, and examples thereof include, but are not limited to, oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes, and it may be formulated into a dosage form suitable for each administration route. Such a dosage form and formulation method may be selected as appropriate from any known dosage forms and methods (see e.g. Hyojun Yakuzaigaku (Standard Pharmaceutics), Ed. by Yoshiteru Watanabe et al., Nankodo, 2003).

Examples of dosage forms suitable for oral administration include, but are not limited to, powder, granule, tablet, capsule, liquid, suspension, emulsion, gel, and syrup, and examples of the dosage form suitable for parenteral administration include injections such as an injectable solution, an injectable suspension, an injectable emulsion, and an injection to be prepared immediately before use. Formulations for parenteral administration may be a form such as an aqueous or nonaqueous isotonic sterile solution or suspension.

The carrier or the composition of the present invention may be supplied in any form, but from the viewpoint of storage stability, it is preferably provided in a form that can be prepared immediately before use, for example in a form that allows a doctor and/or a pharmacist, a nurse, another paramedic, etc. to prepare it at the place of treatment or in the vicinity thereof. In this case, the carrier or the composition of the present invention is provided as one or more containers containing at least one essential constituent element therefor, and it is prepared prior to use, for example, within 24 hours prior to use, preferably within 3 hours prior to use, and more preferably immediately prior to use. When preparing, a reagent, a solvent, preparation equipment, etc. that are normally available in a place of preparation may be used as appropriate.

The present invention therefore also relates to a preparation kit for the carrier or the composition, the kit including one or more containers containing singly or in combination a retinoid, and/or a substance to be delivered, and/or a carrier-constituting substance other than the retinoid, and also to a constituent element necessary for the carrier or the composition provided in the form of such a kit. The kit of the present invention may contain, in addition to the above, instructions, an electronic recording medium such as a CD or DVD related to a process for preparing the carrier and the composition of the present invention, or an administration method, etc. Furthermore, the kit of the present invention may include all of the constituent elements for completing the carrier or the composition of the present invention, but need not always include all of the constituent elements. Therefore, the kit of the present invention need not include a reagent or a solvent that is normally available at a place of medical treatment, an experimental facility, etc. such as, for example, sterile water, physiological saline, or a glucose solution.

The present invention further relates to a method for controlling the activity or growth of an extracellular matrix-producing cell in the lung, or a method for treating pulmonary fibrosis, the method including administering an effective amount of the composition to a subject in need thereof. The effective amount referred to here is, in a method for treating pulmonary fibrosis, for example, an amount that suppresses the onset or recurrence of pulmonary fibrosis, alleviates its symptoms, or delays or stops its progression, and is preferably an amount that prevents the onset or recurrence of pulmonary fibrosis or cures it. It is also preferably an amount that does not cause an adverse effect that exceeds the benefit from administration. Such an amount may be determined as appropriate by an in vitro test using cultured cells or by a test in a model animal such as a mouse, a rat, a dog, or a pig, and such test methods are well known to a person skilled in the art. Moreover, the dose of the retinoid contained in the carrier and the dose of the drug used in the method of the present invention are known to a person skilled in the art, or may be determined as appropriate by the above-mentioned test, etc.

In the method of the present invention, the specific dose of the composition administered may be determined while taking into consideration various conditions with respect to a subject in need of the treatment, such as the severity of symptoms, general health condition of the subject, age, body weight, gender of the subject, diet, the timing and frequency of administration, a medicine used in combination, response to the treatment, compliance with the treatment, etc.

As the administration route, there are various routes including both oral and parenteral routes, and examples thereof include oral, intravenous, intramuscular, subcutaneous, local, intrapulmonary, intra-airway, intratracheal, intrabronchial, nasal, rectal, intraarterial, intraportal, intraventricular, intramedullar, intra-lymph-node, intralymphatic, intrabrain, intrathecal, intracerebroventricular, transmucosal, percutaneous, intranasal, intraperitoneal, and intrauterine routes.

The frequency of administration depends on the properties of the composition used and the above-mentioned conditions of the subject, and may be a plurality of times per day (that is, 2, 3, 4, 5, or more times per day), once a day, every few days (that is, every 2, 3, 4, 5, 6, or 7 days, etc.), a few times per week (e.g. 2, 3, 4 times, etc. per week), every other week, or every few weeks (that is, every 2, 3, 4 weeks, etc.).

In the method of the present invention, the term "subject" means any living individual, preferably an animal, more preferably a mammal, and yet more preferably a human individual. In the present invention, the subject may be healthy or affected by some disorder, and when treatment of pulmonary fibrosis is intended, it typically means a subject affected by interstitial pneumonia or pulmonary fibrosis, or having a risk of being affected by them. For example, when prevention of pulmonary fibrosis is intended, typical examples include, but are not limited to, a subject affected by interstitial pneumonia, in particular by idiopathic interstitial pneumonia.

Furthermore, the term "treatment" includes all types of medically acceptable preventive and/or therapeutic intervention for the purpose of the cure, temporary remission, or prevention of a disorder, etc. For example, the term "treatment" includes medically acceptable intervention of various purposes, including delaying or stopping the progression of pulmonary fibrosis, regression or disappearance of lesions, prevention of onset and prevention of recurrence of pulmonary fibrosis.

The present invention also relates to a method for delivering a drug to an extracellular matrix-producing cell in the lung, utilizing the above carrier. This method includes, but is not limited to, for example, a step of loading a substance to be delivered on the carrier, and a step of administering or adding the carrier having the substance to be delivered carried thereon to a living being or a medium, for example a culture medium, containing an extracellular matrix-producing cell in the lung. These steps may be achieved as appropriate in accordance with any known method or a method described in the present specification, etc. The above delivery method may be combined with another delivery method, for example, another delivery method targeted at the lung. Moreover, the above method includes a mode carried out in vitro and a mode in which an extracellular matrix-producing cell in the lung inside the body is targeted.

EXAMPLES

The present invention is explained in detail by reference to specific examples below, but these specific examples are for illustrative purposes, and do not limit the scope of the present invention.

Example 1

Preparation of siRNA

Three types of siRNA targeted at gp46 (GenBank Accession No. M69246), which is a rat homologue of human HSP47, and a random siRNA control were purchased from Hokkaido System Science Co., Ltd. Each siRNA consists of 27 bases overhanging on the 3' side, and the sequences are as follows.

```
Sequence A:
                              (sense, SEQ ID NO: 1)
5'-GUUCCACCAUAAGAUGGUAGACAACAG-3'

(antisense, SEQ ID NO: 2)
5'-GUUGUCUACCAUCUUAUGGUGGAACAU-3'

Sequence B:
                              (sense, SEQ ID NO: 3)
5'-CCACAAGUUUUAUAUCCAAUCUAGCAG-3'

(antisense, SEQ ID NO: 4)
5'-GCUAGAUUGGAUAUAAAACUUGUGGAU-3'

Sequence C:
                              (sense, SEQ ID NO: 5)
5'-CUAGAGCCAUUACAUUACAUUGACAAG-3'

(antisense, SEQ ID NO: 6)
5'-UGUCAAUGUAAUGUAAUGGCUCUAGAU-3'

Random siRNA:
                              (sense, SEQ ID NO: 7)
5'-CGAUUCGCUAGACCGGCUUCAUUGCAG-3'

(antisense, SEQ ID NO: 8)
5'-GCAAUGAAGCCGGUCUAGCGAAUCGAU-3'
```

Furthermore, siRNA that was labeled on the 5' side with the fluorescent dye 6'-carboxyfluorescein (6-FAM) was also prepared.

Example 2

Preparation of siRNA-Containing VA-Bound Liposome

As a liposome, a cationic liposome containing DC-6-14, cholesterol, and DOPE at a molar ratio of 4:3:3 (Lipotrust, Hokkaido System Science Co., Ltd.) was used. 10 nmol of liposome and 20 nmol of vitamin A (VA: all-trans retinol, Sigma) were mixed in DMSO using a 1.5-mL tube, then dissolved in chloroform, evaporated once, and then suspended in PBS (phosphate buffered saline). Subsequently, the siRNA (10 μg/mL) obtained in Example 1 and the liposome suspension were mixed at a ratio of 1:1 (w/w). Free VA and siRNA contained in the liposome suspension thus obtained were removed by a micropartition system (Sartorion VIVASPIN 5000MWCO PES), thus giving an siRNA-containing VA-bound liposome (VA-lip-siRNA). The amount of VA added and the amount of VA contained in the purified liposome were measured by HPLC, and the proportion of VA bound to the liposome was examined; as a result, it was found that the majority of the VA (95.6±0.42%) was bound to the liposome. Furthermore, the efficiency of uptake of siRNA into the liposome was measured by RiboGreen assay (Molecular Probes), and it was as high as 94.4±3.0%. Here, in this formulation, VA was at least partially exposed on the surface of the formulation.

Example 3

In Vivo Anti-Pulmonary-Fibrosis Activity of siRNA-Containing VA-Bound Liposome (1) Induction of Pulmonary Fibrosis and Administration of Drug Male S-D rats (6 rats/group, 4 weeks old, Charles River Laboratories Japan, Inc.) were administered once with 0.5 mg bleomycin (BLM) dissolved in 0.5 cc of physiological saline into the lung intratracheally by intratracheal cannulation under anesthesia, to produce a bleomycin pulmonary fibrosis model. With this method, a significant fibrosis occurs in the lung generally after approximately 3 weeks. The VA-lip-siRNA prepared in Example 2 (0.75 mg/kg as an amount of siRNA, 1 ml/kg in volume, i.e., 200 μl for a rat of 200 g) or PBS (1 ml/kg in volume) was administered to the rats via the tail vein, starting from the day of administration of bleomycin, at a frequency of 3 times/week. The rats were sacrificed 21 days after the bleomycin administration, and bronchoalveolar lavage (BAL) fluid was analyzed, hydroxyproline in the lung was quantified, and histological investigation of the lung tissue was performed (see FIG. 1). Student's t-test was used for the evaluation of statistically-significant difference.

(2) Analysis of BAL Fluid

Figure 2:
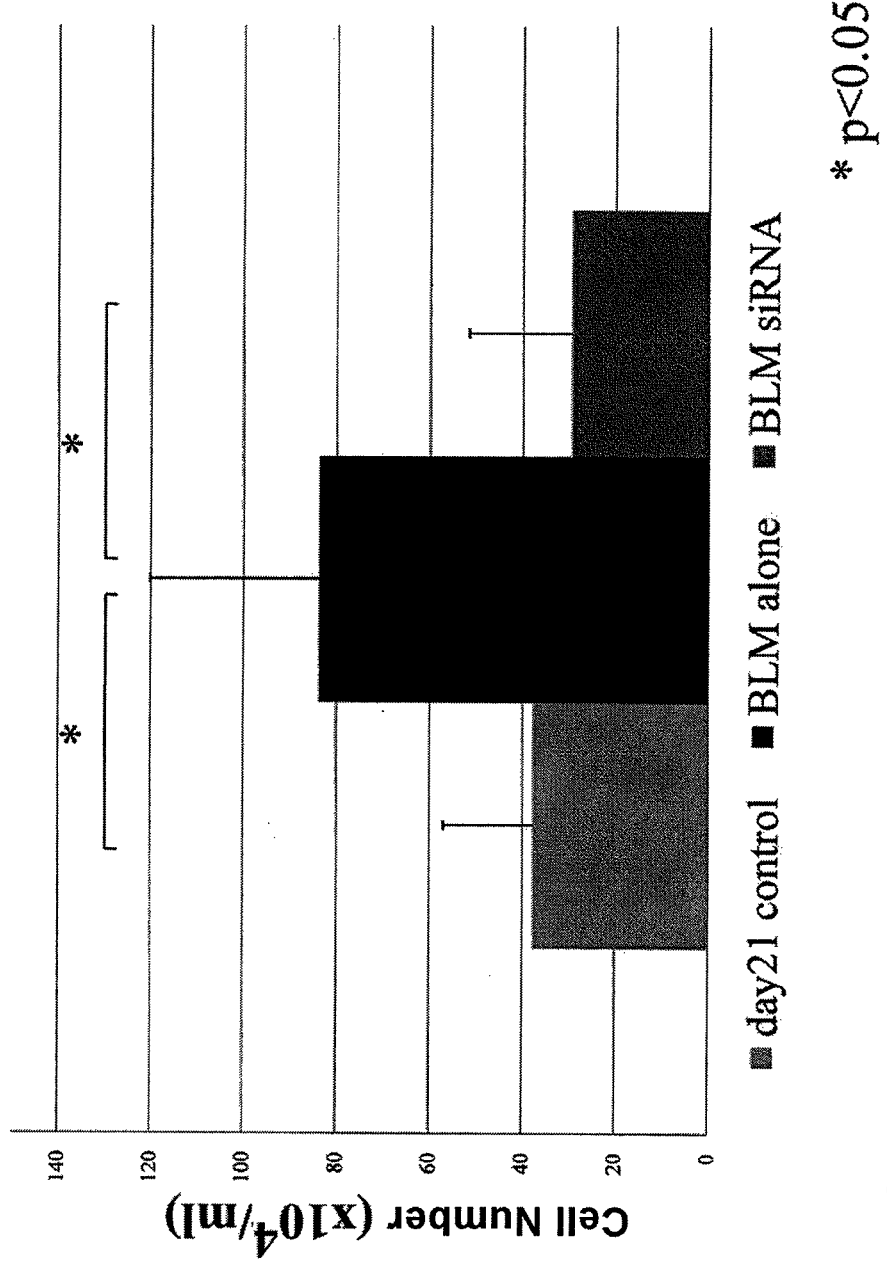
FIG. 2 is a graph showing the total number of cells in BAL liquid on day 21 after administration of bleomycin. "Control" means normal rats without administration of bleomycin.

Analysis of BAL was performed as follows. The rats were intraperitoneally administered with a lethal dose of pentobarbital sodium, their thorax was opened, then the trachea was exposed and a cannula was inserted into the trachea. Subsequently, 7 ml of physiological saline was injected into the lung via the tracheal cannula and the lavage fluid was collected. This process of injection and collection was repeated 5 times, and the collected lavage fluids were combined and centrifuged at 250× g for 10 min. The total number of cells was counted using a cytometer, and cell fraction count was performed using a May-Giemsa stained cytospin smear preparation. At least 200 cells were counted and classified into macrophage, eosinophil, neutrophil, and lymphocyte in accordance with general morphological criteria. Results of the total cell number count were shown in FIG. 2. This figure shows that the number of cells in the BAL fluid of the VA-lip-siRNA administration group (BLM siRNA) significantly decreased to the level similar to that of the normal control rat administered with PBS instead of bleomycin, compared to the PBS administration group (BLM alone); suggesting that inflammation has been improved.

(3) Quantification of Hydroxyproline in Lung Tissue

Figure 3:
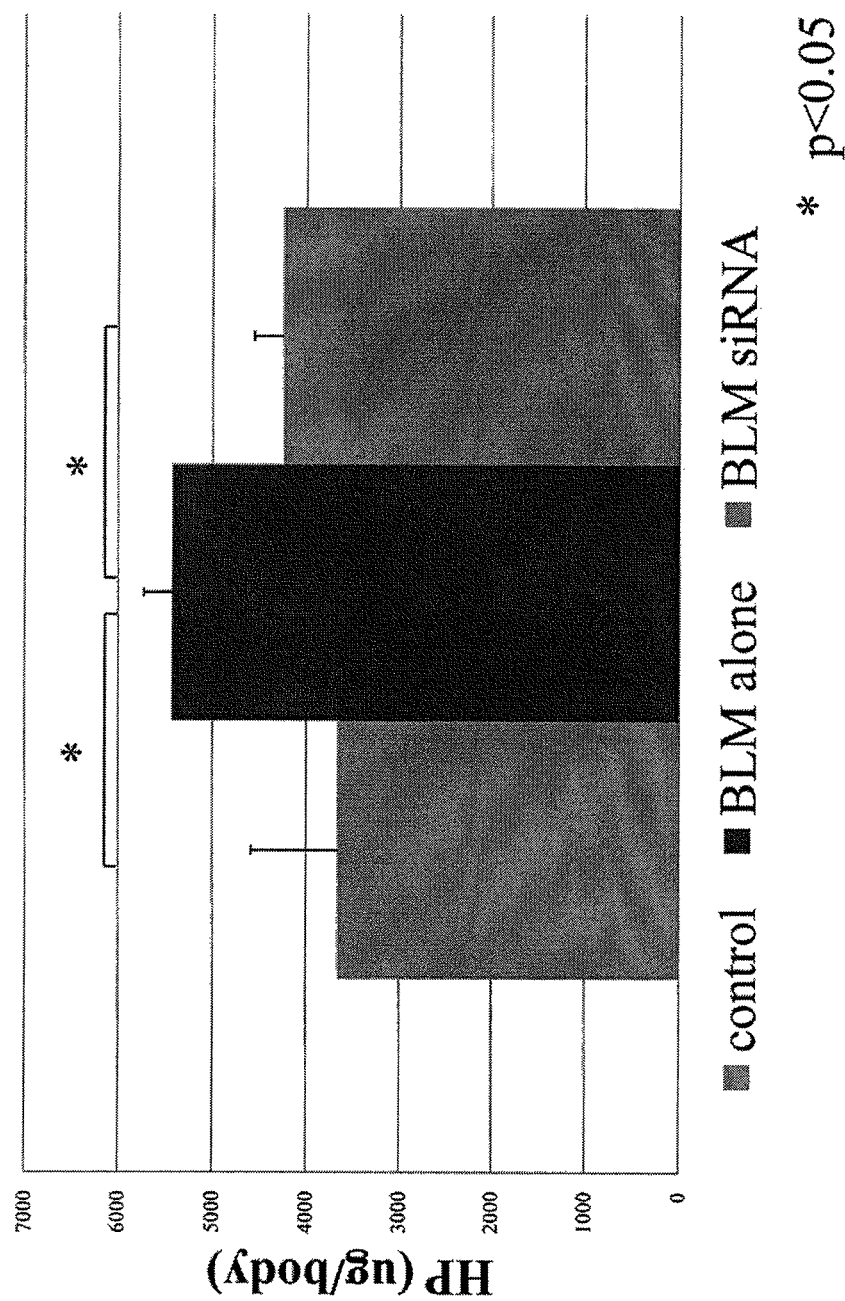
FIG. 3 is a graph showing the amount of hydroxyproline (HP) in the lung on day 21 after administration of bleomycin. "Control" means normal rats without administration of bleomycin.

The lung was removed from the rats after BAL, then one whole lung was homogenized using a polytron homogenizer, and the lung hydroxyproline was quantified using a method of Kivirikko, et al. (Kivirikko K I, et al. Analytical Biochemistry 1967; 19: 249-255). Namely, the lung tissue was homogenized in 6-N hydrochloric acid at 110° C. for 18 hr, and 25-μ aliquot was dried at 60° C. It was then dissolved in 1.2 ml of 50% isopropanol, incubated with acetate citrate, pH 6.0, and 200 ml of 0.56% chloramine-T solution at room temperature for 10 min, followed by an incubation at 50° C. for 90 min after the addition of 1 ml of Ehrilich solution; then absorbance at 560 nm was measured. Results shown in FIG. 3 indicate that the amount of lung hydroxyproline (μg) of the VA-lip-siRNA administration group (BLM siRNA) significantly decreased compared to that of the PBS administration group (BLM alone), suggesting that the fibrosis of the lung was significantly suppressed.

(4) Histological Investigation

Figure 4:
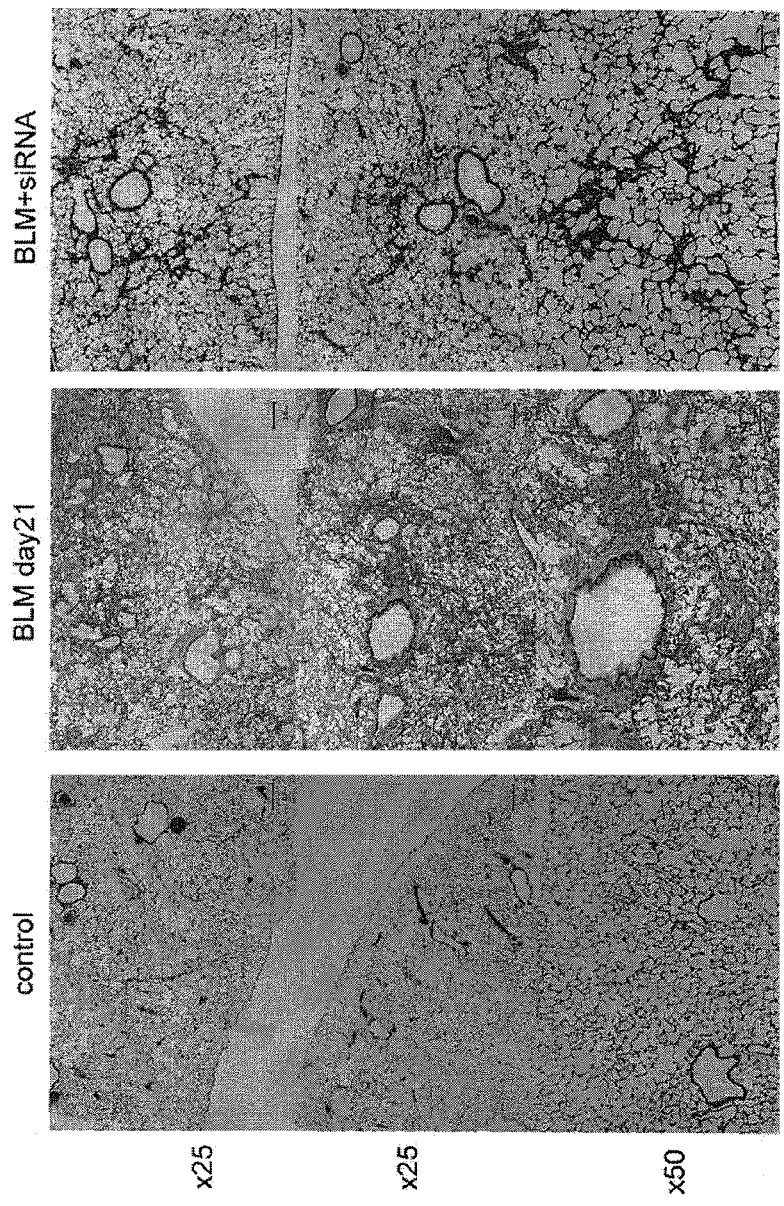
FIG. 4 shows photographs of HE-stained lung tissues on day 21 after administration of bleomycin.
Figure 5:
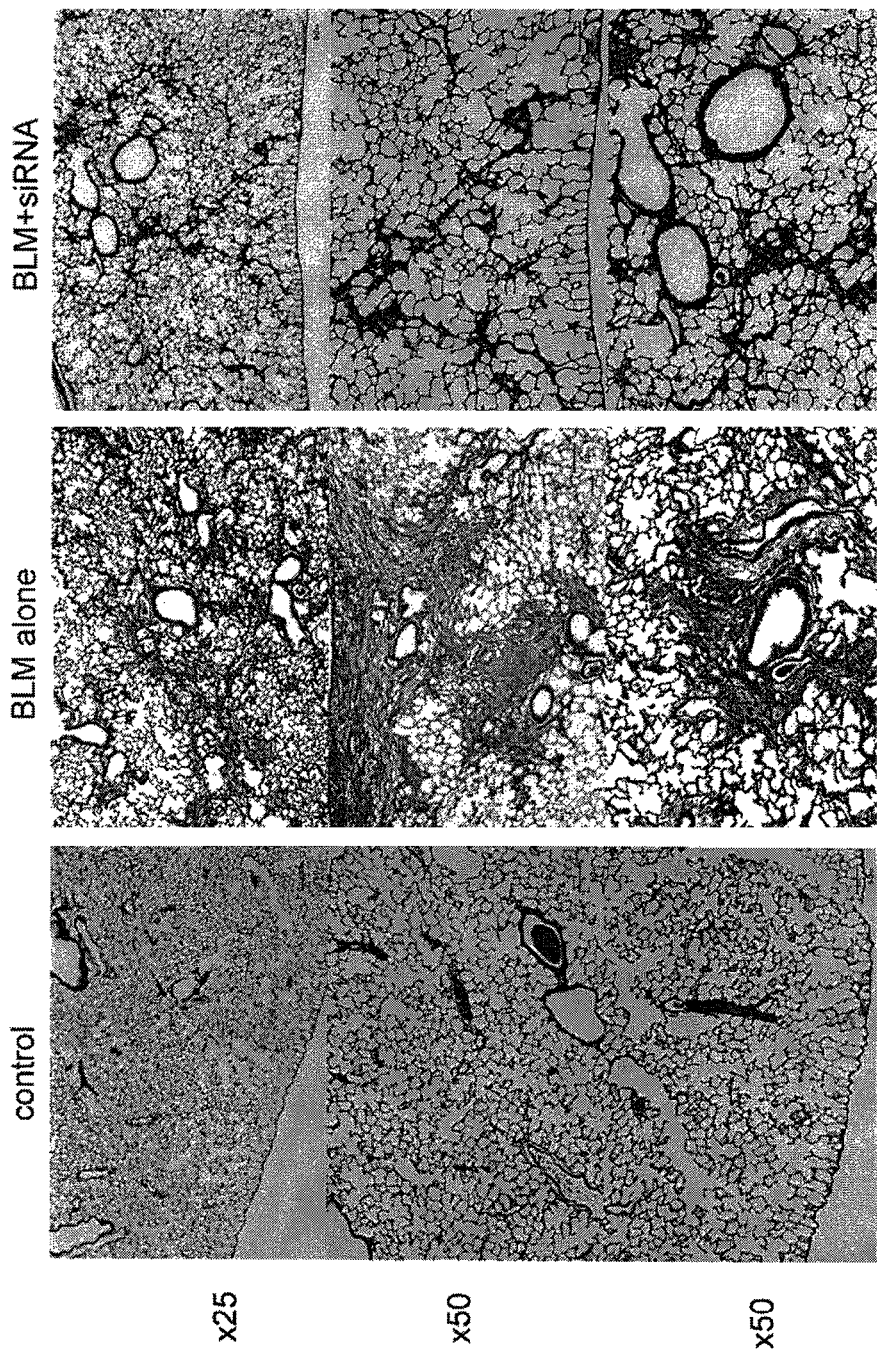
FIG. 5 shows photographs of Azan-stained lung tissues on day 21 after administration of bleomycin.
Figure 6:
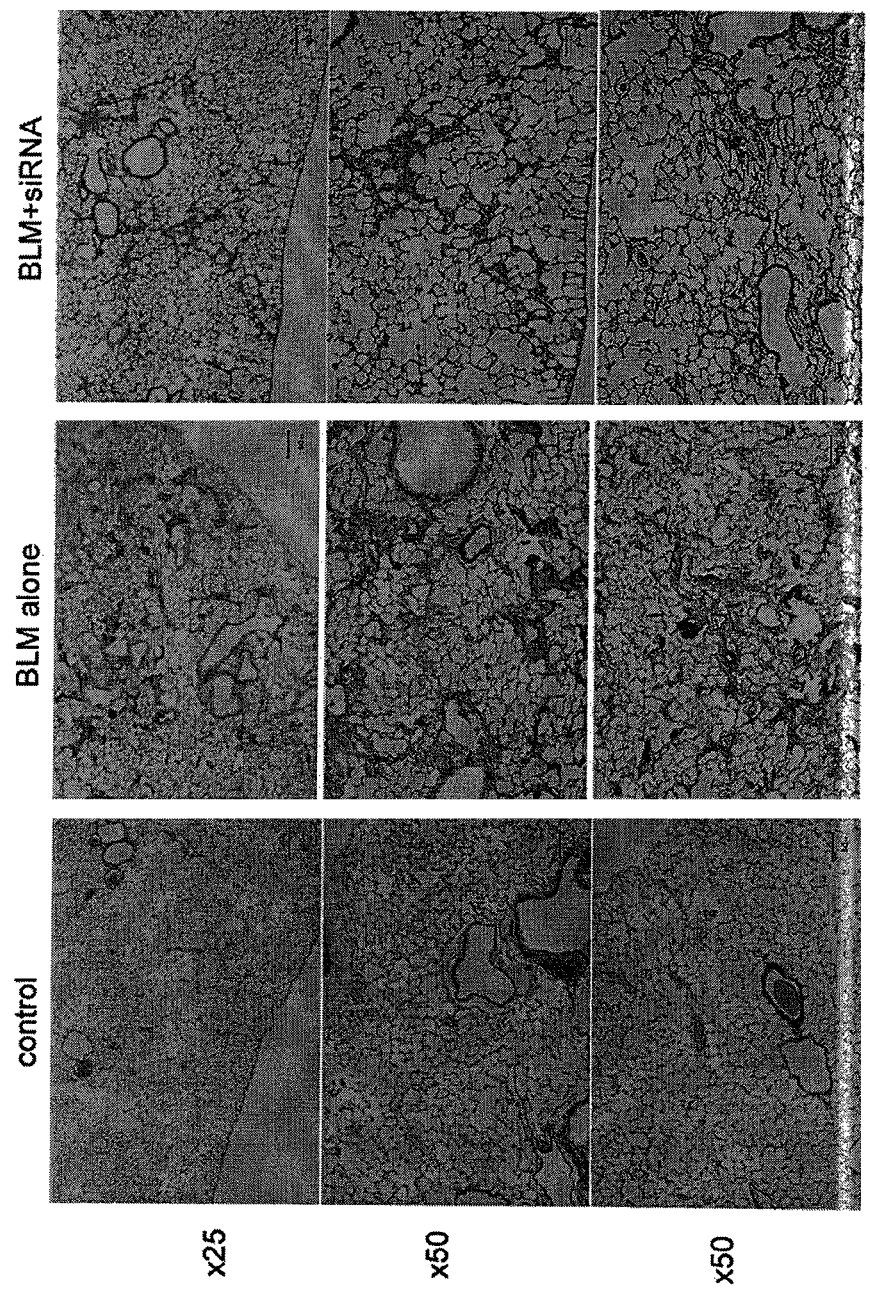
FIG. 6 shows photographs showing distribution of αSMA-positive cells in the lung tissues on day 21 after administration of bleomycin.

A part of the removed lung was formalin-fixed in accordance with a routine method, and subjected to hematoxylin-eosin (HE) staining, azan staining (azocarmine, aniline blue orange G solution), or immunostaining with anti-αSMA antibody. Regarding the immunostaining, after deparaffinization, samples were reacted with a mouse anti-αSMA antibody (Nichirei Corporation, clone 1A4) as a primary antibody, then with a peroxidase-labeled anti-mouse IgG as a secondary antibody, and developed with DAB. As shown by the results of HE staining in FIG. 4, in the PBS administration group (BLM day 21), findings characteristic to pulmonary fibrosis such as disappearance of pulmonary alveoli, bleeding images and interstitial hyperplasia were observed, whereas in the VA-lip-siRNA administration group (BLM+siRNA), fibrotic lesions were significantly improved. Similarly, as shown by the results of the azan staining in FIG. 5, in the PBS administration group (BLM alone), a noticeable fibrotic image characterized by enlargement of interstice due to a large quantity of blue-stained collagenous fibrils was observed, whereas in the VA-lip-siRNA administration group (BLM+siRNA), fibrosis were apparently suppressed. Moreover, as shown by the results of the αSMA staining in FIG. 6, while a large number of αSMA-positive cells having a brown color were observed in the interstice in the PBS administration group (BLM alone), the number of αSMA-positive cells significantly decreased in the VA-lip-siRNA administration group (BLM+siRNA).

Considering that siRNA basically acts in the cytoplasm, the above results indicate that the retinoid functioned as a targeting agent to extracellular matrix-producing cells in the lung, so that a drug is efficiently delivered to these cells, leading to a significant improvement in disease states of pulmonary fibrosis.

Example 4

In Vivo Anti-Pulmonary-Fibrosis Activity of siRNA-Containing VA-Bound Liposome (Liposome Formulation)

(1) Induction of Pulmonary Fibrosis and Administration of Drug

Male S-D rats (8 rats/group, 8 weeks old, Charles River Laboratories Japan, Inc.) were administered once with 0.45 mg bleomycin (BLM) dissolved in 0.1 mL of saline into the lung by intratracheal spray (MicroSprayer®, Penn-Century, Inc.) under anesthesia, to produce a bleomycin pulmonary fibrosis model. With this method, a significant fibrosis occurs in the lung generally after approximately 2 weeks. This pulmonary fibrosis model allows better histological evaluation, as the fibrosis occurs uniformly in the entire lung field without difference between right lung and left lung as well as between the upper part and the lower part of the lung; provides long lasting fibrotic lesions which allow to more accurately evaluate not only prophylactic, but also therapeutic effects of a treatment; presents less individual variability in the elicitation of fibrosis; and allows to cover fibrosis occurring principally in subpleural region which causes clinical problems in human.

Figure 7:
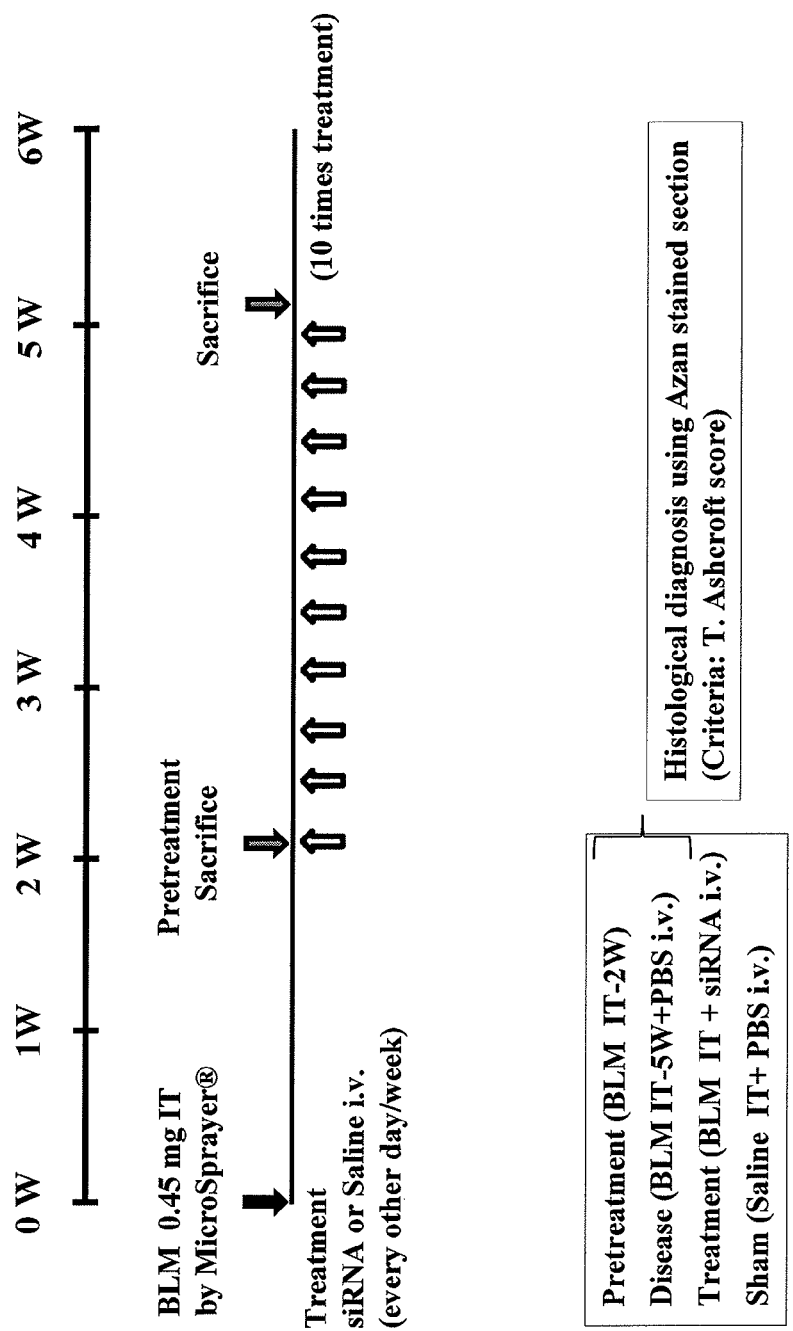
FIG. 7 is a schematic diagram showing induction of pulmonary fibrosis in rats by intratracheal spray of bleomycin and drug-administration schedule.

The Liposome formulation (1.5 mg/kg as an amount of siRNA, 1 ml/kg in volume, i.e., 200 μl for a rat of 200 g) or PBS (1 ml/kg in volume) was administered to the rats via the tail vein, starting from the 2 weeks after the bleomycin administration, for total of ten times (every other day). The rats were sacrificed at two days post last treatment, histological investigation of the lung tissue was performed (see FIG. 7). One-way ANOVA and Bonferroni multi comparison test was used for the evaluation of statistically significant difference.

Figure 8:
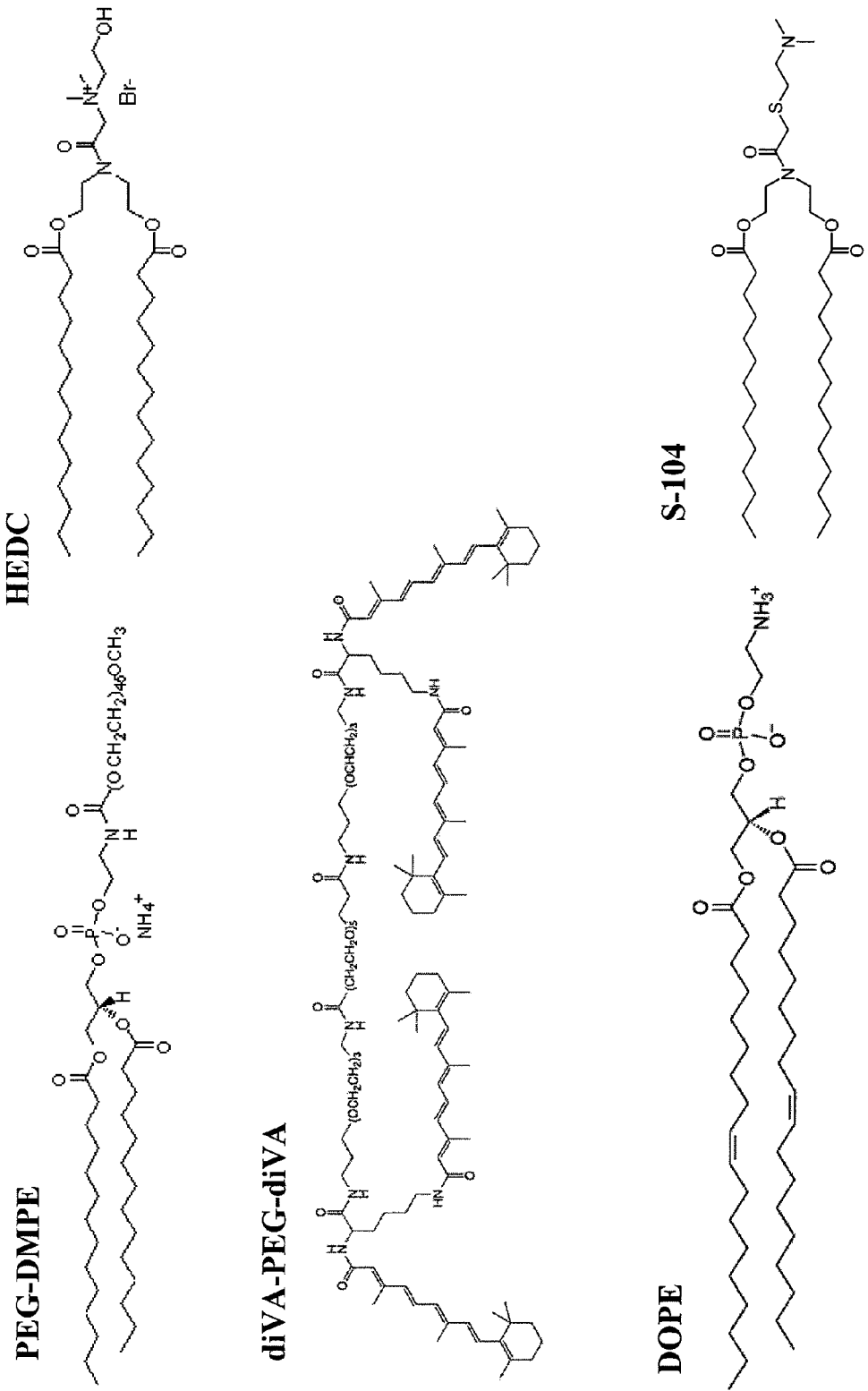
FIG. 8 shows the structural formula of HEDC, S-104, DOPE, PEG-DMPE and diVA-PEG-diVA.

The composition of the liposome was HEDC/S-104/DOPE/Cholesterol/PEG-DMPE/diVA-PEG-diVA (20:20:30:25:5:2 Molar %; see FIG. 8 for the structural formula of HEDC, S-104, DOPE, PEG-DMPE and diVA-PEG-diVA). Details of siRNA were as follows:

PS strand:

(SEQ ID NO: 9)
5'-idAB-rG-rA-rG-rA-rC-rA-rC-rA-rU-rG-rG-rG-rUrG-25rC-25rU-25rA-25rU-25rA-C3-P-3'

GS strand:

(SEQ ID NO: 10)
5'-mU-rA-mU-rA-mG-rC-25rA-rC-mC-rC-mA-rU-mG-rUmG-rU-mC-rU-mC-C3-C3-3' wherein:
rX represents ribonucleotides;
mX represents 2'-O-Methyl ribonucleotides;
25rX represents ribonucleotides with 2'-5' linkages;
C3 represents a 1,3-propanediol spacer;
idAB represents inverted 1,2-dideoxy-D-Ribose;
P represents a phosphate group on the 3'-terminus;
The 3'-terminus C3 is introduced by support-loaded 1,3-propanediol spacer;
The 3'-terminus phosphate group (P) is introduced by the use of support-loaded diethyl sulfonyl (Pi) spacer.

(2) Histological Investigation

Figure 9:
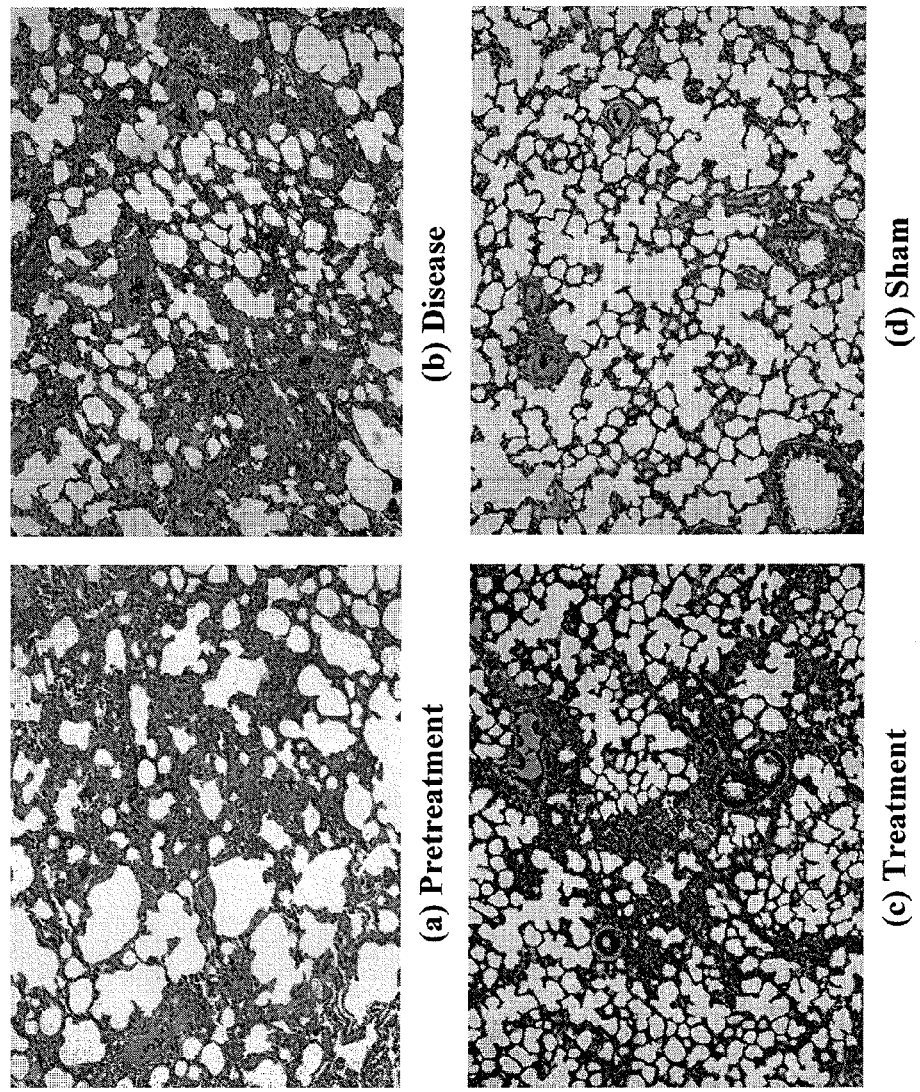
FIG. 9 shows photographs of representative lung field of Azan-stained sections of each group at a magnification of 80×. (a) Pretreatment (BLM IT-2W), (b) Disease (BLM IT-5W+PBS i.v.), (c) Treatment (BLM IT+siRNA i.v.), (d) Sham (Saline-IT+PBS i.v.).

A part of the removed lung was formalin-fixed in accordance with a routine method, and subjected to azan staining (azocarmine, aniline blue orange G solution). As shown by the results of the azan staining in FIG. 9, in the PBS administration group (Disease), a noticeable fibrotic image characterized by enlargement of interstice due to a large quantity of blue-stained collagenous fibrils was observed, whereas in the formulation administration group (Treatment), fibrosis were apparently suppressed.

Figure 10:
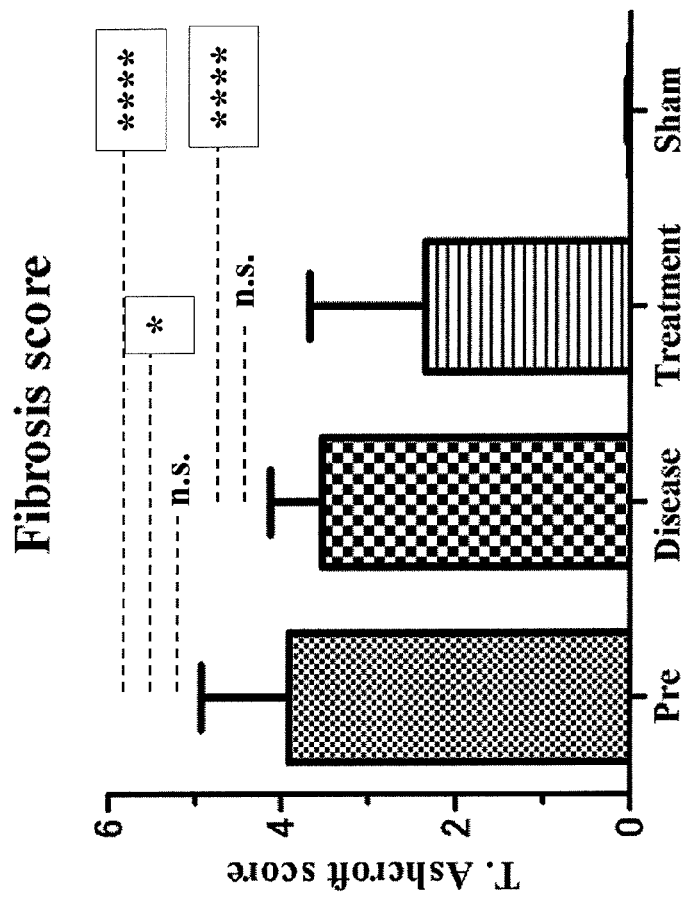
FIG. 10 is a graph showing the results of histological scoring (T. Ashcroft score) of Azan-stained section for each group. 20 randomly selected both lung fields were evaluated under 80× magnification for each rat. Statistical analysis were performed by One-Way ANOVA Bonferroni multi comparison test using Prism5 software. $*p<0.05$, $****p<0.0001$, n.s.: not significant.

As shown by the results of histological scoring (T. Ashcroft score) in FIG. 10, in the formulation administration group (Treatment), fibrosis score was significantly decreased compared to the state before the treatment (Pretreatment).

What is claimed is:

1. A composition for treating pulmonary fibrosis, comprising a substance delivery carrier that comprises an amount of a retinoid targeting agent that is effective to specifically target the substance delivery carrier to extracellular matrix-producing cells in the lung and a drug that controls the activity or growth of extracellular matrix-producing cells in the lung, wherein the drug that controls the activity or growth of extracellular matrix-producing cells in the lung is selected from the group consisting of an siRNA, a ribozyme, an anti-sense nucleic acid, and a DNA/RNA chimeric polynucleotide which target HSP47.

2. The composition of claim 1, wherein the drug is an siRNA.

3. The composition of claim 1, wherein the drug is a ribozyme.

4. The composition of claim 1, wherein the drug is an anti-sense nucleic acid.

5. The composition of claim 1, wherein the drug is a DNA/RNA chimeric polynucleotide.

6. The composition of claim 1, wherein the retinoid comprises retinol.

* * * * *

UNITED STATES PATENT AND TRADEMARK OFFICE
CERTIFICATE OF CORRECTION

PATENT NO. : 8,574,623 B2
APPLICATION NO. : 13/648543
DATED : November 5, 2013
INVENTOR(S) : Niitsu et al.

It is certified that error appears in the above-identified patent and that said Letters Patent is hereby corrected as shown below:

On the Title Page

In column 1 (page 5, item 30, Foreign Application Priority Data) at line 3, Change "Mar. 14, 2008" to --Mar. 17, 2008--.

In column 2 (page 1, item 56) at line 45, Under Other Publications, change "protion" to --proton--.

In column 2 (page 1, item 56) at line 47, Under Other Publications, change "mannosa" to --mannose--.

In column 1 (page 3, item 56) at line 24, Under Other Publications, change "oligodeoxpucleotides," to --oligodeoxynucleotides,--.

In column 1 (page 3, item 56) at line 40, Under Other Publications, change "Nonmenclature" to --Nomenclature--.

In column 1 (page 3, item 56) at line 45, Under Other Publications, change "of21" to --of 21--.

In column 2 (page 3, item 56) at line 49, Under Other Publications, change "dimentylnitrosame" to --dimethylnitrosamine--.

In column 2 (page 3, item 56) at line 51, Under Other Publications, change "ofliposomes," to --of liposomes,--.

In column 2 (page 3, item 56) at line 55, Under Other Publications, change "phosphateyinsulin-like" to --phosphate/insulin-like--.

In column 2 (page 4, item 56) at line 66, Under Other Publications, change "gene-slicing" to --gene-silencing--.

In column 2 (page 4, item 56) at line 69, Under Other Publications, change "M5076-heptatic" to --M5076-hepatic--.

Signed and Sealed this
Tenth Day of June, 2014

Michelle K. Lee
*Deputy Director of the United States Patent and Trademark Office*

CERTIFICATE OF CORRECTION (continued)
U.S. Pat. No. 8,574,623 B2

In column 1 (page 5, item 56) at line 7, Under Other Publications, change "ofliposomes" to --of liposomes--.

In column 1 (page 5, item 56) at line 18, Under Other Publications, change "ofliver" to --of liver--.

In column 1 (page 5, item 56) at line 20, Under Other Publications, change "Drosphila" to --Drosophila--.

In column 1 (page 5, item 56) at line 23, Under Other Publications, change "Polylysine-Retinalddehyde" to --Polylysine-Retinaldehyde--.

In column 1 (page 5, item 56) at line 24, Under Other Publications, change "Bilogical" to --Biological--.

In column 1 (page 5, item 56) at line 25, Under Other Publications, change "imortalized" to --immortalized--.

In column 1 (page 5, item 56) at lines 38-39, Under Other Publications, change "UDP glucoronyltransferease," to --UDP-glucuronyltransferase,--.

In column 2 (page 5, item 56) at line 1, Under Other Publications, change "ofliposomes" to --of liposomes--.

In column 2 (page 5, item 56) at line 17, Under Other Publications, change "Apoptpsis-inducing" to --Apoptosis-inducing--.

In column 2 (page 5, item 56) at line 26, Under Other Publications, change "receptorg-selective" to --receptor-selective--.

In the Specification

In column 4 at lines 59-60, Change "acitretine," to --acitretin,--.

In column 5 at line 16, Change "acitretine," to --acitretin,--

In column 8 at line 50, Change "mycoplasmal" to --mycoplasma--.